(12) United States Patent
Zhou et al.

(10) Patent No.: US 10,072,287 B2
(45) Date of Patent: *Sep. 11, 2018

(54) METHODS OF TARGETED SEQUENCING

(75) Inventors: Wei Zhou, Saratoga, CA (US); Rui Mei, Santa Clara, CA (US); Hajime Matsuzaki, Cupertino, CA (US)

(73) Assignee: Centrillion Technology Holdings Corporation (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/395,417

(22) PCT Filed: Sep. 10, 2010

(86) PCT No.: PCT/US2010/048526
§ 371 (c)(1),
(2), (4) Date: Oct. 23, 2012

(87) PCT Pub. No.: WO2011/032040
PCT Pub. Date: Mar. 17, 2011

(65) Prior Publication Data
US 2013/0045872 A1    Feb. 21, 2013

Related U.S. Application Data

(60) Provisional application No. 61/241,378, filed on Sep. 10, 2009.

(51) Int. Cl.
*C12Q 1/6869* (2018.01)
*C12Q 1/6827* (2018.01)

(52) U.S. Cl.
CPC ................. *C12Q 1/6827* (2013.01)

(58) Field of Classification Search
CPC ............. C12Q 1/68; C07H 21/04; C12N 9/93
See application file for complete search history.

(56) References Cited

U.S. PATENT DOCUMENTS 4,437,975 A    3/1984   Gillespie et al.
4,458,066 A    7/1984   Caruthers et al.
(Continued)

FOREIGN PATENT DOCUMENTS

DE    10149786 A1    7/2003
DE    10214395 A1    10/2003
(Continued)

OTHER PUBLICATIONS

"How many species of bacteria are there" (wisegeek.com; accessed Sep. 23, 2011).*
(Continued)

*Primary Examiner* — Narayan Bhat
(74) *Attorney, Agent, or Firm* — Wilson Sonsini Goodrich & Rosati

(57) ABSTRACT

The present invention provides methods for targeted sequencing of polynucleotide. In one aspect, the present invention provides a method of sequencing a target polynucleotide with fewer probes. In another aspect, the present invention provides a method of sequencing a target polynucleotide with longer reads. Locus-specific, ligation-assisted sequencing/genotyping method and ligation-captured sequencing method are also provided in the present invention. The methods of the present invention allow low-cost, high-throughput and accurate sequencing of nucleic acids.

19 Claims, 14 Drawing Sheets
Specification includes a Sequence Listing.

(56) References Cited

U.S. PATENT DOCUMENTS

| | | | |
|---|---|---|---|
| 4,469,863 A | 9/1984 | Ts'o et al. |
| 4,683,195 A | 7/1987 | Mullis et al. |
| 4,683,202 A | 7/1987 | Mullis |
| 4,883,750 A | 11/1989 | Whiteley et al. |
| 4,988,617 A | 1/1991 | Landegren et al. |
| 5,034,506 A | 7/1991 | Summerton et al. |
| 5,143,854 A | 9/1992 | Pirrung et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,386,023 A | 1/1995 | Sanghvi et al. |
| 5,409,818 A | 4/1995 | Davey et al. |
| 5,413,909 A | 5/1995 | Bassam et al. |
| 5,470,705 A | 11/1995 | Grossman et al. |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,602,240 A | 2/1997 | De Mesmaeker et al. |
| 5,631,734 A | 5/1997 | Stern et al. |
| 5,637,684 A | 6/1997 | Cook et al. |
| 5,644,048 A | 7/1997 | Yau |
| 5,705,628 A | 1/1998 | Hawkins |
| 5,756,285 A | 5/1998 | Fuller |
| 5,800,992 A | 9/1998 | Fodor et al. |
| 5,834,758 A | 11/1998 | Trulson et al. |
| 5,837,832 A | 11/1998 | Chee et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,902,723 A | 5/1999 | Dower et al. |
| 5,936,324 A | 8/1999 | Montagu |
| 5,981,956 A | 11/1999 | Stern |
| 6,025,139 A | 2/2000 | Yager et al. |
| 6,025,601 A | 2/2000 | Trulson et al. |
| 6,045,996 A | 4/2000 | Cronin et al. |
| 6,063,603 A | 5/2000 | Davey et al. |
| 6,090,555 A | 7/2000 | Fiekowsky et al. |
| 6,141,096 A | 10/2000 | Stern et al. |
| 6,185,030 B1 | 2/2001 | Overbeck |
| 6,201,639 B1 | 3/2001 | Overbeck |
| 6,214,246 B1 | 4/2001 | Craighead |
| 6,218,803 B1 | 4/2001 | Montagu et al. |
| 6,225,625 B1 | 5/2001 | Pirrung et al. |
| 6,267,872 B1 | 7/2001 | Akeson et al. |
| 6,361,947 B1 | 3/2002 | Dong et al. |
| 6,386,749 B1 | 5/2002 | Watts et al. |
| 6,391,592 B1 | 5/2002 | Su et al. |
| 6,391,623 B1 | 5/2002 | Besemer et al. |
| 6,401,267 B1 * | 6/2002 | Drmanac ............ C12Q 1/6874 |
| | | 4/356 |
| 6,410,276 B1 | 6/2002 | Burg et al. |
| 6,440,662 B1 | 8/2002 | Gerwen et al. |
| 6,464,842 B1 | 10/2002 | Goloychenko et al. |
| 6,518,189 B1 | 2/2003 | Chou |
| 6,548,810 B2 | 4/2003 | Zaluzec et al. |
| 6,582,938 B1 | 6/2003 | Su et al. |
| 6,627,067 B1 | 9/2003 | Branton et al. |
| 6,632,611 B2 | 10/2003 | Su et al. |
| 6,673,615 B2 | 1/2004 | Denison et al. |
| 6,685,841 B2 | 2/2004 | Lopez et al. |
| 6,787,308 B2 | 9/2004 | Balasubramanian et al. |
| 6,833,246 B2 | 12/2004 | Balasubramanian |
| 6,852,487 B1 | 2/2005 | Barany et al. |
| 6,872,529 B2 | 3/2005 | Su et al. |
| 6,897,023 B2 | 5/2005 | Fu et al. |
| 6,958,225 B2 | 10/2005 | Dong et al. |
| 6,969,488 B2 | 11/2005 | Bridgham et al. |
| 7,001,724 B1 | 2/2006 | Greenfield |
| 7,094,531 B1 * | 8/2006 | Schmidt ............ C12Q 1/6872 |
| | | 382/129 |
| 7,189,503 B2 | 3/2007 | Akeson et al. |
| 7,217,562 B2 | 5/2007 | Cao et al. |
| 7,238,485 B2 | 7/2007 | Akeson et al. |
| 7,258,838 B2 | 8/2007 | Li et al. |
| 7,267,966 B2 | 9/2007 | Dong et al. |
| 7,297,778 B2 | 11/2007 | Matsuzaki et al. |
| 7,300,788 B2 | 11/2007 | Matsuzaki et al. |
| 7,689,022 B2 | 3/2010 | Weiner et al. |
| 9,328,382 B2 | 5/2016 | Drmanac et al. |
| 9,689,032 B2 | 6/2017 | Zhou et al. |
| 2002/0012930 A1 | 1/2002 | Rothberg et al. |
| 2003/0022207 A1 | 1/2003 | Balasubramanian et al. |
| 2003/0044781 A1 | 3/2003 | Korlach et al. |
| 2003/0058629 A1 | 3/2003 | Hirai et al. |
| 2003/0064376 A1 | 4/2003 | Makarov et al. |
| 2003/0064398 A1 | 4/2003 | Barnes |
| 2003/0100102 A1 | 5/2003 | Rothberg et al. |
| 2003/0148344 A1 | 8/2003 | Rothberg et al. |
| 2003/0186279 A1 | 10/2003 | Kennedy et al. |
| 2003/0186280 A1 | 10/2003 | Kennedy et al. |
| 2004/0072217 A1 | 4/2004 | Kennedy et al. |
| 2004/0106130 A1 | 6/2004 | Besemer et al. |
| 2004/0248144 A1 | 12/2004 | Mir |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0186576 A1 | 8/2005 | Chan et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0275782 A1 | 12/2006 | Gunderson et al. |
| 2007/0031942 A1 * | 2/2007 | Gao ...................... C07H 21/04 |
| | | 435/91.2 |
| 2007/0065816 A1 | 3/2007 | Doug et al. |
| 2007/0128649 A1 | 6/2007 | Young |
| 2008/0102504 A1 | 5/2008 | Akeson et al. |
| 2008/0171316 A1 | 7/2008 | Golovchenko et al. |
| 2008/0248561 A1 | 10/2008 | Golovchenko et al. |
| 2009/0005252 A1 * | 1/2009 | Drmanac ............ C12Q 1/6837 |
| | | 506/3 |
| 2009/0018024 A1 | 1/2009 | Church et al. |
| 2009/0088327 A1 | 4/2009 | Rigatti et al. |
| 2009/0203085 A1 | 8/2009 | Kurn et al. |
| 2009/0291475 A1 | 11/2009 | Lao et al. |
| 2010/0029498 A1 | 2/2010 | Gnirke et al. |
| 2010/0143900 A1 | 6/2010 | Peluso et al. |
| 2010/0297706 A1 | 11/2010 | Lee et al. |
| 2011/0009276 A1 | 1/2011 | Vermaas et al. |
| 2012/0083417 A1 | 4/2012 | Zhou et al. |
| 2012/0252682 A1 | 10/2012 | Zhou et al. |
| 2014/0065604 A1 | 3/2014 | Zhou et al. |
| 2014/0186940 A1 | 7/2014 | Goel |
| 2014/0315724 A1 | 10/2014 | Zhou et al. |
| 2016/0046985 A1 | 2/2016 | Drmanac et al. |
| 2016/0168632 A1 | 6/2016 | Edwards |
| 2016/0237486 A1 | 8/2016 | Zhou et al. |
| 2017/0022554 A1 | 1/2017 | Drmanac et al. |
| 2018/0010180 A1 | 1/2018 | Zhou et al. |

FOREIGN PATENT DOCUMENTS

| | | |
|---|---|---|
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| GB | 2398383 A | 8/2004 |
| WO | WO 88/10315 A1 | 12/1988 |
| WO | WO 90/06995 A1 | 6/1990 |
| WO | WO95/04160 * | 2/1995 |
| WO | WO-9640999 A1 | 12/1996 |
| WO | WO 98/44152 A1 | 10/1998 |
| WO | WO 99/47964 A1 | 9/1999 |
| WO | WO-0132930 A1 | 5/2001 |

(56) References Cited

FOREIGN PATENT DOCUMENTS

| WO | WO-0229003 A2 | 4/2002 |
|---|---|---|
| WO | WO-02088382 A2 | 11/2002 |
| WO | WO-03020968 A2 | 3/2003 |
| WO | WO-03031947 A2 | 4/2003 |
| WO | WO-2005044836 A3 | 7/2007 |
| WO | WO-2008066245 A1 | 6/2008 |
| WO | WO-2009097626 A2 | 8/2009 |
| WO | WO-2010075188 A2 | 7/2010 |
| WO | WO-2011032040 A1 | 3/2011 |
| WO | WO-2012040624 A1 | 3/2012 |
| WO | WO-2012106546 A2 | 8/2012 |
| WO | WO-2012134602 A2 | 10/2012 |
| WO | WO-2012106546 A3 | 11/2013 |
| WO | WO-2015017759 A1 | 2/2015 |

OTHER PUBLICATIONS

"Plant," (Wikipedia.com; accessed Mar. 8, 2013).*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"List of sequenced bacterial genomes" (Wikipedia.com; accessed Jan. 24, 2014).*
Mir et al, Sequencing by Cyclic Ligation and Cleavage (CycLiC) directly on a microarray captured template, 2009, 37, e5, pp. 1-8 (Year: 2009).*
Office action dated Apr. 14, 2016 for CN Application No. CN201080050858.9 with English summary.
U.S. Appl. No. 09/916,135, filed Jul. 25, 2001, Matsuzaki et al.
U.S. Appl. No. 60/011,359, filed Feb. 9, 1996, Barany et al.
U.S. Appl. No. 60/364,731, filed Mar. 15, 2002, Weiner et al.
Dempcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.
Dong, et al. Flexible use of high-density oligonucleotide arrays for single-nucleotide polymorphism discovery and validation. Genome Res. Aug. 2001;11(8):1418-24.
Grossman, et al. High-density multiplex detection of nucleic acid sequences: oligonucleotide ligation assay and sequence-coded separation. Nucleic Acids Res. Oct. 25, 1994;22(21):4527-34.
Hacia, et al. Resequencing and mutational analysis using oligonucleotide microarrays. Nat Genet. Jan. 1999;21(1 Suppl):42-7.
International search report and written opinion dated Nov. 22, 2010 for PCT/US2010/048526.
Kidd, et al. Mapping and sequencing of structural variation from eight human genomes. Nature. May 1, 2008;453(7191):56-64.
Letsinger, et al. Effects of pendant groups at phosphorus on binding properties of d-ApA analogues. Nucleic Acids Res. Apr. 25, 1986;14(8):3487-99.
Mag, et al. Synthesis and selective cleavage of an oligodeoxynucleotide containing a bridged internucleotide 5'-phosphorothioate linkage. Nucleic Acids Res. Apr. 11, 1991;19(7):1437-41.
Newton, et al. The production of PCR products with 5' single-stranded tails using primers that incorporate novel phosphoramidite intermediates. Nucleic Acids Res. Mar. 11, 1993;21(5):1155-62.
Schultz, et al. Single-target molecule detection with nonbleaching multicolor optical immunolabels. Proc Natl Acad Sci U S A. Feb. 1, 2000;97(3):996-1001.
Sprinzl, et al. Enzymatic incorporation of ATP and CTP analogues into the 3' end of tRNA. Eur J Biochem. Dec. 1997;81(3):579-89.
Turcatti, et al. A new class of cleavable fluorescent nucleotides: synthesis and optimization as reversible terminators for DNA sequencing by synthesis. Nucleic Acids Res. Mar. 2008;36(4):e25.

Adams, et al. The Genome Sequence of *Drosophila melanogaster*. Science. Mar. 24, 2000; 287 (5461): 2185-2195.
Bentley et al. Accurate whole human genome sequencing using reversible terminator chemistry. Nature 456(7218):53-59 (2008).
Constans, et al. Beyond Sanger: Toward the $1,000 Genome, The Scientist. Jun. 30, 2003; 17(13): 36.
Egholm et al. PNA hybridizes to complementary oligonucleotides obeying the Watson-Crick hydrogen-bonding rules. Nature 365(6446):566-568 (1993).
European office action dated Aug. 12, 2015 for EP Application No. 11827648-4.
European search report and search opinion dated May 15, 2014 for EP Application No. 11827648.4.
European search report and written opinion dated Sep. 10, 2014 for EP Application No. 12762821.2.
Gao, et al. Oligonucleotide synthesis using solution photogenerated acids. J. Am. Chem. Soc. 1999; 120: 12,698-12699.
Gao et al. Unusual conformation of a 3'-thioformacetal linkage in a DNA duplex. J. Biomolecular NMR.34:17-34 (1994).
Guo, et al. Four-color DNA sequencing with 3'-0-modified nucleotide reversible terminators and chemically cleavable fluorescent dideoxynucleotides. Proc Natl Acad Sci U S A. 2008. 105(27):9145-50. Epub Jun. 30, 2008.
How many species of bacteria are there (wisegeek.com; accessed Jan. 21, 2014).
International search report and written opinion dated Jan. 18, 2012 for PCT/US2011/053079.
International search report and written opinion dated Oct. 1, 2012 for PCT/US2012/000185.
Ivashuta, et al. Linear amplification coupled with controlled extension as a means of probe amplification in a cDNA array and gene expression analysis during cold acclimation in alfalfa (*Medicago sativa* L.). J Exp Bot. Feb. 2002; 53(367): 351-9.
Jenkins et al. The Biosynthesis of Carbocyclic Nucleosides Chem Soc Re 24:169-176 (1995).
Levene, et al. Zero-mode waveguides for single-molecule analysis at high concentrations. Science. Jan. 31, 2003;299(5607):682-6.
Marguiles, et al. Genome sequencing in microfabricated high-density picolitre reactors. Nature. Sep. 15, 2005;437(7057):376-80. Epub Jul. 31, 2005.
Metzker, ML. Sequencing technologies—the next generation. Nat Rev Genet. 2010.11(1):31-46 Epub Dec. 8, 2009. Review.
Miller, et al. (1988) Nucleic Acids Research, 16(3): 9-10.
Murinae, (Wikipedia.com, accessed Mar. 18, 2013).
Nickerson et al. Automated DNA diagnostics using an ELISA-based oligonucleotide ligation assay. PNAS USA 87(22):8923-8927 (1990).
Notice of allowance dated Feb. 22, 2017 for U.S. Appl. No. 13/970,321.
Office action dated Jan. 22, 2017 for CN Application No. 201280027272X with English.
Office action dated Feb. 13, 2015 for CN Application No. 201180056235.7 (with English translation).
Office action dated Feb. 19, 2013 for U.S. Appl. No. 13/153,218.
Office action dated Mar. 13, 2013 for U.S. Appl. No. 13/243,833.
Office action dated Apr. 6, 2017 for U.S. Appl. No. 14/009,089.
Office action dated Apr. 30, 2014 for CN Application No. 201180056235.7 (with English translation).
Office action dated May 12, 2016 for EP Application No. 12762821.2.
Office action dated Jun. 14, 2017 for U.S. Appl. No. 14/970,435.
Office action dated Jun. 18, 2015 for CN Application No. 201280027272X.
Office action dated Jun. 29, 2015 for U.S. Appl. No. 13/243,833.
Office action dated Jun. 29, 2016 for CN Application No. 201280027272X with English.
Office action dated Jul. 27, 2012 for U.S. Appl. No. 13/243,833.
Office action dated Aug. 3, 2017 for EP Application No. 12762821.2.
Office action dated Sep. 27, 2016 for U.S. Appl. No. 13/970,321.
Office action dated Sep. 28, 2015 for U.S. Appl. No. 13/970,321.
Office action dated Sep. 29, 2015 for CN Application No. 201180056235.7.

(56) References Cited

OTHER PUBLICATIONS

Office action dated Nov. 17, 2014 for U.S. Appl. No. 13/970,321.
Office Action dated Dec. 12, 2017 for U.S. Appl. No. 15/631,414.
Plant, (Wikipedia.com; accessed Mar. 8, 2013).
Rawls. Optimistic about antisense. Promising clinical results and chemical strategies for further improvements delight antisense drug researchers. C & E News. 35-59 (Jun. 2, 1997).
Ronaghi, M. Pyrosequencing sheds light on DNA sequencing. Genome Res. Jan. 2001; 11(1): 3-11. Review.
Seo, et al. Four-color DNA sequencing by synthesis on a chip using photocleavable fluorescent nucleotides. Proc. Natl. Acad. Sci. USA. Apr. 26, 2005; 102(17):5926-5931.
Venter, et al. The Sequence of the Human Genome. Science. Feb. 16, 2001;291(5507):1304-51.
Virus, Wikipedia.com, accessed Apr. 18, 2012.
Wu, et al. 3'-O-modified nucleotides as revers . . . [Proc Natl Acad Sci U S A. 2007]—PubMed—NCBI. Proc Natl Acad Sci U S A. Oct. 16, 2007;104(42):16462-7. Epub Oct. 8, 2007.
Yang, et al. Nucleoside alpha-thiotriphosphates, polymerases and the exonuclease III analysis of oligonucleotides containing phosphorothioate linkages. Nucleic Acids Res. 2007;35(9):3118-27. Epub Apr. 22, 2007.
U.S. Appl. No. 15/631,414 Office Action dated May 18, 2018.

\* cited by examiner

|   | 1 | 2 | 3 | 4 | 5 | 6 | 7 | 8 | 9 | 10 |   |
|---|---|---|---|---|---|---|---|---|---|----|---|
| Maternal | A | T | C | G | C | T | A | T | C | G | same as Reference |
| Paternal | A | T | C | G | A | T | C | T | C | G | 3 base INSERTION |
| Forward Probe Reads | A | T | C | G | C/A | T/T | A/C | T/C | C/T | G/A |   |

|   | 1 | 2 | 3 | 4 | 5 | 6 | 7 | 8 | 9 | 10 |   |
|---|---|---|---|---|---|---|---|---|---|----|---|
| Maternal | A | T | C | G | C | T | A | T | C | G | same as Reference |
| Paternal | A | T | C | G | A | T | C | T | C | G | 3 base INSERTION |
| Reverse Probe Reads | A/G | T/A | C/T | G/C | C | T | A | T | C | G |   |

FIG. 6

| Gene | Variation | Alleles | Ref | rs_id | build36_position |
|---|---|---|---|---|---|
| CYP2C9 | *6 | -/A | A | rs9333131 | chr10:96699029 |
| CYP344 | *6 | -/A | - | rs4646438 | chr7:99201970-99201971 |
| CYP246 | *9 | G/T | T | rs28399433 | chr19:46048219 |
| ABCB1 | T4238ntC | C/T | T | rs1128503 | chr7:87017537 |
| CYP2C9 | *4 | Del/Het | Dipl | | chr19:46012070-48842089 |

*FIG. 8A*

Forward Probes

AATCAATGGACATGAACAACCCTCAGGACTTTATTGATTGCTTCCTGATG
ATCAATGGACATGAACAACCCTCAGGACTTTATTGATTGCTTCCTGATGA
TCAATGGACATGAACAACCCTCAGGACTTTATTGATTGCTTCCTGATGAA
CAATGGACATGAACAACCCTCAGGACTTTATTGATTGCTTCCTGATGAAA
AATGGACATGAACAACCCTCAGGACTTTATTGATTGCTTCCTGATGAAAA

GCCCTCAGAAACACTCTGGTTACCTTTGTGGGACTCAGTTTCTTTTGAAT
CCCTCAGAAACACTCTGGTTACCTTTGTGGGACTCAGTTTCTTTTGAATT
CCTCAGAAACACTCTGGTTACCTTTGTGGGACTCAGTTTCTTTTGAATTC
CTCAGAAACACTCTGGTTACCTTTGTGGGACTCAGTTTCTTTTGAATTCT
TCAGAAACACTCTGGTTACCTTTGTGGGACTCAGTTTCTTTTGAATTCTG

TGAGGCCAGCATGGTGGTAGTGGGATGATAGATGGTGACGGCTGGGGTGG
GAGGCCAGCATGGTGGTAGTGGGATGATAGATGGTGACGGCTGGGGTGGT
AGGCCAGCATGGTGGTAGTGGGATGATAGATGGTGACGGCTGGGGTGGTT
GGCCAGCATGGTGGTAGTGGGATGATAGATGGTGACGGCTGGGGTGGTTT
GCCAGCATGGTGGTAGTGGGATGATAGATGGTGACGGCTGGGGTGGTTTG

CCACAGCCACTGTTTCCAACCAGGGCCACCGTCTGCCCACTCTGCACCTT
CACAGCCACTGTTTCCAACCAGGGCCACCGTCTGCCCACTCTGCACCTTC
ACAGCCACTGTTTCCAACCAGGGCCACCGTCTGCCCACTCTGCACCTTCA
CAGCCACTGTTTCCAACCAGGGCCACCGTCTGCCCACTCTGCACCTTCAG
AGCCACTGTTTCCAACCAGGGCCACCGTCTGCCCACTCTGCACCTTCAGG

AGGTGTAGCAATGGGAGGTTTAGATGTCCTTTCCTGCCAGGTACACTTGC
GGTGTAGCAATGGGAGGTTTAGATGTCCTTTCCTGCCAGGTACACTTGCA
GTGTAGCAATGGGAGGTTTAGATGTCCTTTCCTGCCAGGTACACTTGCAA
TGTAGCAATGGGAGGTTTAGATGTCCTTTCCTGCCAGGTACACTTGCAAA
GTAGCAATGGGAGGTTTAGATGTCCTTTCCTGCCAGGTACACTTGCAAAT

*FIG. 8B*

Reverse Probes

TCAACAAATCACAAATTCACAAGCAGTCACATAACTAAGCTTTTGTTTAC
CAACAAATCACAAATTCACAAGCAGTCACATAACTAAGCTTTTGTTTACA
AACAAATCACAAATTCACAAGCAGTCACATAACTAAGCTTTTGTTTACAT
ACAAATCACAAATTCACAAGCAGTCACATAACTAAGCTTTTGTTTACATT
CAAATCACAAATTCACAAGCAGTCACATAACTAAGCTTTTGTTTACATTT

TCAGTGAAATTTCTCTTTTGCTTCTAGCACCGAGTGGATTTCCTTCAGC
CAGTGAAATTTCTCTTTTGCTTCTAGCACCGAGTGGATTTCCTTCAGCT
AGTGAAATTTCTCTTTTGCTTCTAGCACCGAGTGGATTTCCTTCAGCTG
GTGAAATTTCTCTTTTGCTTCTAGCACCGAGTGGATTTCCTTCAGCTGA
TGAAATTTCTCTTTTGCTTCTAGCACCGAGTGGATTTCCTTCAGCTGAT

GAGGTGAAATGAGGTAATTATGTAATCAGCCAAAGTCCATCCCTCTTTTT
AGGTGAAATGAGGTAATTATGTAATCAGCCAAAGTCCATCCCTCTTTTTC
GGTGAAATGAGGTAATTATGTAATCAGCCAAAGTCCATCCCTCTTTTTCA
GTGAAATGAGGTAATTATGTAATCAGCCAAAGTCCATCCCTCTTTTTCAG
TGAAATGAGGTAATTATGTAATCAGCCAAAGTCCATCCCTCTTTTTCAGG

CTGTGTCTGTGAATTGCCTTGAAGTTTTTTTCTCACTCGTCCTGGTAGAT
TGTGTCTGTGAATTGCCTTGAAGTTTTTTTCTCACTCGTCCTGGTAGATC
GTGTCTGTGAATTGCCTTGAAGTTTTTTTCTCACTCGTCCTGGTAGATCT
TGTCTGTGAATTGCCTTGAAGTTTTTTTCTCACTCGTCCTGGTAGATCTT
GTCTGTGAATTGCCTTGAAGTTTTTTTCTCACTCGTCCTGGTAGATCTTG

AGGAGATGACGGCACAGCAGTCATATTTGCAAGTGTACCTGGCAGGAAAG
GGAGATGACGGCACAGCAGTCATATTTGCAAGTGTACCTGGCAGGAAAGG
GAGATGACGGCACAGCAGTCATATTTGCAAGTGTACCTGGCAGGAAAGGA
AGATGACGGCACAGCAGTCATATTTGCAAGTGTACCTGGCAGGAAAGGAC
GATGACGGCACAGCAGTCATATTTGCAAGTGTACCTGGCAGGAAAGGACA

*FIG. 8C*

METHODS OF TARGETED SEQUENCING

RELATED APPLICATIONS

This application claims the benefit of U.S. Provisional Application No. 61/241,378, filed Sep. 10, 2009, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Oct. 15, 2013, is named 38558-702.831 SL.txt and is 12,964 bytes in size.

BACKGROUND OF THE INVENTION

Large-scale multiplex analysis of highly polymorphic loci is needed for practical identification of individuals, e.g., for paternity testing and in forensic science (Reynolds et al., Anal. Chem., 63:2-15 (1991)), for organ-transplant donor-recipient matching (Buyse et al., Tissue Antigens, 41:1-14 (1993) and Gyllensten et al., PCR Meth. Appl, 1:91-98 (1991)), for genetic disease diagnosis, prognosis, and prenatal counseling (Chamberlain et al., Nucleic Acids Res., 16:11141-11156 (1988) and L. C. Tsui, Human Mutat., 1:197-203 (1992)), and the study of drug metabolism and oncogenic mutations (Hollstein et al., Science, 253:49-53 (1991)). In addition, the cost-effectiveness of infectious disease diagnosis by nucleic acid analysis varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, and then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 to Mullis, et al. and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported. U.S. Pat. No. 4,883,750 to N. M. Whiteley, et al., D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, "Genetic Disease Detection and DNA Amplification Using Cloned Thermostable Ligase," Proc. Nat'l Acad. Sci. USA, 88:189-93 (1991) and F. Barany, "The Ligase Chain Reaction (LCR) in a PCR World," PCR Methods and Applications, 1:5-16 (1991).

Another scheme for multiplex detection of nucleic acid sequence differences is disclosed in U.S. Pat. No. 5,470,705 to Grossman et. al. where sequence-specific probes, having a detectable label and a distinctive ratio of charge/translational frictional drag, can be hybridized to a target and ligated together. This technique was used in Grossman, et. al., "High-density Multiplex Detection of Nucleic Acid Sequences: Oligonucleotide Ligation Assay and Sequence-coded Separation," Nucl. Acids Res. 22(21):4527-34 (1994) for the large scale multiplex analysis of the cystic fibrosis transmembrane regulator gene.

Jou, et. al., "Deletion Detection in Dystrophia Gene by Multiplex Gap Ligase Chain Reaction and Immunochromatographic Strip Technology," Human Mutation 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

Solid-phase hybridization assays require multiple liquid-handling steps, and some incubation and wash temperatures must be carefully controlled to keep the stringency needed for single-nucleotide mismatch discrimination. Multiplexing of this approach has proven difficult as optimal hybridization conditions vary greatly among probe sequences.

Ligation of allele-specific probes generally has used solid-phase capture (U. Landegren et al., Science, 241:1077-1080 (1988); Nickerson et al., Proc. Natl. Acad. Sci. USA, 87:8923-8927 (1990)) or size-dependent separation (D. Y. Wu, et al., Genomics, 4:560-569 (1989) and F. Barany, Proc. Natl. Acad. Sci, 88:189-193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step-polymerase extension. The use of probes with distinctive ratios of charge/translational frictional drag for a more complex multiplex will either require longer electrophoresis times or the use of an alternate form of detection.

There is a great need for a rapid, high-throughput, and low-cost assay format that allows targeted sequencing with high specificity. Most sequence methods do not distinguish between the multiple copies of DNA that organisms may have. For example, human genome contains DNA sequences of both maternal and paternal origin. Therefore, polymorphisms may exist at loci and provide multiple different readings at the same locus during standard sequencing methods, complicating the sequencing process. The present invention permits reading one copy of DNA at regions containing variations, such as single nucleotide polymorphisms (SNPs).

SUMMARY OF THE INVENTION

In one aspect, the present invention provides a locus-specific sequencing method which utilizes genotyping steps to attain enhanced specificity. In one embodiment, the present invention provides a method of sequencing comprising forming a hybridization complex, which comprises a first set of capture probes, a target polynucleotide, and a first solution probe. At least one of the first capture probes binds a first region of the target polynucleotide. The first solution probe binds a second region of the target polynucleotide. The first solution probe has a base at the 3' end complementary to a first loci site of the target polynucleotide. Therefore, when hybridization occurs at least one of the first set of capture probes and the first solution probe may be ligated. Additionally, the first solution probe comprises a cleavable first cap. This method includes ligating at least one of the first set of capture probes and the first solution probe, adding a second cap to those capture probes of the first set of capture probes not ligated to the first solution probe, removing the first cap, and then sequencing the target polynucleotide.

In some embodiments, the method further comprises forming a hybridization complex comprising a second solution probe that hybridizes to the target polynucleotide, wherein the second solution probe binds to a third region of the target polynucleotide, wherein the second solution probe has a base complementary to a second loci site of the target polynucleotide. The second solution probe may be ligated to the first solution probe. The method includes forming a hybridization complex comprising a third solution probe that hybridizes to the target polynucleotide. The third solution probe binds to a fourth region of the target polynucleotide, has a base complementary to a third loci site of the target polynucleotide and comprises a universal primer sequence. This aspect of the invention also involves ligating the third solution probe to the second solution probe, removing the target polynucleotide, and sequencing the target polynucleotide with a primer that hybridizes the universal primer sequence of the third solution probe.

In some embodiments, the sequencing comprises placing the target-probe hybridization complex under nucleic acid synthesis conditions in the presence of free nucleotides to allow extension of the probe that is complementary to the target polynucleotide.

In some embodiments, the method further comprises removing non-specific hybridization.

In some embodiments, the first cap comprises a capping dye and the first solution probe comprises a cleavage site. In one aspect the second cap comprises a protection group.

In some embodiments, the first set of capture probes is attached to a flat surface or a bead. In one aspect, the flat surface is a flow cell. In some embodiments, the first set of capture probes is synthesized or spotted on said flat surface. In some embodiments, the first set of capture probes is spotted randomly at a controlled density. In some embodiments, the first set of capture probes is spotted at known locations on the flat surface.

In some embodiments, the first set of capture probes comprises polynucleotides. In some embodiments, the each capture probe of said first set of capture probes contains 50-150 nucleotides.

In some embodiments, the first, second, or third solution probe comprises a polynucleotide. In one aspect, the first, second, or third solution probe contains 5 to 50 nucleotides. In some embodiments, the target polynucleotide comprises a single nucleotide polymorphism (SNP), an insertion or deletion, or a copy number variation.

In some embodiments, the target polynucleotide is removed from the hybridization duplex.

In some embodiments, the first set of capture probes comprises allele-specific capture probes for a locus. In some embodiments, the allele-specific capture probes are to known alleles of the first loci.

In some embodiments, a nucleotide reversible terminator is added to the hybridization complex as a first cap. In some embodiments, the nucleotide reversible terminator contains an amino-2-hydroxypropyl group.

In some embodiments, at least 50% of a genome is sequenced using no more than 500 million probes. In another aspect, 99.5% of the genome is sequenced. In some embodiments, the nucleic acid sequence of the first, second or third solution probe is known. In some embodiments, the number of total probes used is about 5 million to 500 million. In another aspect, the number of duplicate probes is less and 5. In some embodiments, multiple loci in the genome are sequenced. In some embodiments, the sequencing avoids SNP with minor allele frequency of greater than 0.05 at the extreme 3' end of the first, second, third or fourth solution probe or first or second capture probe sequences. In some embodiments, sequencing said target polynucleotide comprises generating reads that are greater than 5-50 bases.

In some embodiments, the first, second, third or fourth solution probe is labeled. In some embodiments, the first, second, third or fourth solution probe has at least one base that is degenerate. In some embodiments, sequencing information of the target polynucleotide or genome is obtained via a computer system. In some embodiments, the computer system comprises an algorithm for detecting, processing, analyzing and/or assembling nucleotide sequence information.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows the representative steps of ligation captured sequencing.

FIG. 6 shows a schematic on reading heterozygous insertions/deletions. The top panel shows "in situ" array feature in which the probes have both maternal and paternal chromosomes hybridized (SEQ ID NOS 1-3, respectively, in order of appearance). The bottom panel shows that on a "lawn" flow cell, each probe will have either maternal or paternal chromosome hybridized (SEQ ID NOS 4-6, respectively, in order of appearance).

FIG. 8A-C shows probe design sequences for five example loci from the PharmaADME panel (PharmaADME.org). Each locus is represented by sets of five overlapping probe sequences in both the forward and reverse orientations. The five loci include examples of a deletion, insertion, copy number, and two SNP variants (FIG. 8A). The probe sequences for the copy number example at CYP2A6 were modified from a primer sequence described in Fukami et al 2006 (*Pharmacogenomics Journal* 6: 401-412). FIG. 8B discloses "Forward_Probes" as SEQ ID NOS 7-31 and FIG. 8C discloses "Reverse_Probes" as SEQ ID NOS 32-56, all respectively, in order of appearance.

DETAILED DESCRIPTION OF THE INVENTION

Figure 1:
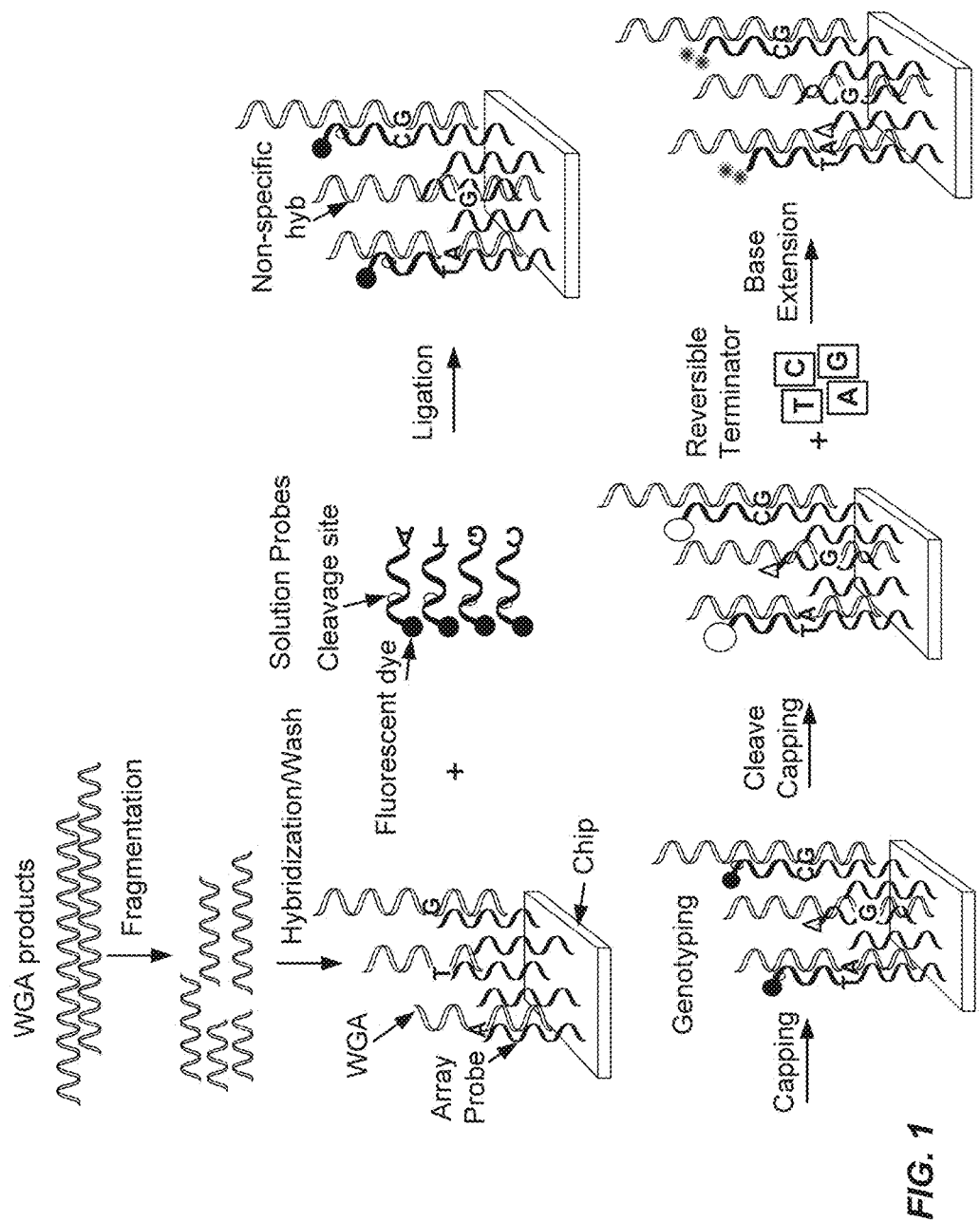
FIG. 1 shows the representative steps of ligation assisted sequencing.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, N.Y.; Gait, "Oligonucleotide Synthesis: A Practical Approach" 1984, IRL Press, London, Nelson and Cox (2000), Lehninger, (2004) Principles of Biochemistry 4$^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

The present invention provides a locus-specific sequencing method which utilizes genotyping steps to attain enhanced specificity.

In one aspect, the present invention provides a method of sequencing comprising: (1) forming a hybridization complex, which comprises a first set of capture probes, a target polynucleotide, and a first solution probe, at least one of the first capture probes binds a first region of the target polynucleotide, the first solution probe binds a second region of the target polynucleotide, the first solution probe has a base at the 3' end complementary to a first loci site of the target polynucleotide so that when hybridization occurs at least one of the first set of capture probes and the first solution probe may be ligated; (2) ligating at least one of the first set of capture probes and the first solution probe; (3) adding a second cap to those capture probes of the first set of capture probes not ligated to the first solution probe; (4) optionally removing the first cap; and (5) sequencing the target polynucleotide. The first solution probe preferably comprises a cleavable first cap.

In another aspect, the present invention provides a method for sequencing a genome or at least 50% of a genome using no more than 5 million, 10 million, 50 million, 100 million, 150 million, 200 million, 500 million capture probes. In some embodiments, at least 50%, 85%, 95%, 99.0%, 99.1%, 99.2%, 99.3%, 99.4%, 99.5%, 99.6%, 99.7%, 99.8%, 99.9% or more of the genome is sequenced. In one embodiment, the genome is a human genome. In some embodiments, the capture probes used in the subject methods are loci-specific and allele specific. The loci can contain a single nucleotide polymorphism (SNP), an insertion or deletion, or a copy number variation. For example, the loci can contain a drug metabolizing enzyme and transporter gene. In some embodiments, the nucleic acid sequences of the capture probes are known. In some embodiments, the capture probes can have a sequence located next to a loci of interest or proximate to the loci at no more than 5, 10, 15, 20, 25, 30, 35, 40, 45, 50, 100 bases distance.

In some embodiments, the present invention provides a method of performing a genomic sequencing reaction using approximately 0, 1, 2, 3, 4, 5, or more duplicated capture probes. In some embodiments, the same locus may be covered by multiple different capture probes and each locus will generally have at least one, but more likely at least two capture probes for biallelic feature such as a SNP. In one example, the number of duplicate capture probes is 0. In some embodiments, multiple loci in the genome are sequenced. In some embodiments, multiple alleles in the genome are sequenced. The sequencing may avoid SNP with minor allele frequency of >0.05 at extreme 3' end of probe sequences. In some embodiments, the capture probe contains 10-10,000 nucleotides, for example, a capture probe can be 50 nucleotides. The capture probes can be located at known geographic locations or random geographic locations at a controlled density on a substrate, such as a solid phase support (e.g. a flat surface or a bead).

In another aspect, the present invention also provides a method for sequencing a target polynucleotide by generating reads that are greater 5, 10, 15, 20, 30, 40, 50, 60, 74, 100, 150 bases. In some embodiments, a lawn of randomly placed capture probes is used, wherein each capture probe generates a read greater than 5, 10, 15, 20, 30, 40, 50, 60, 74, 100, 150 bases. In some embodiments, the read is greater than 10, 11, 12, 13, 14, 15, 16, 17, 18, 19 or 20 bases. Loci-specific and/or allele-specific capture probes can be used. These capture probes can be located at known or random geographic locations on a substrate. In some embodiments, the target polynucleotide is genomic DNA, for example, human genomic DNA. Multiple loci and/or alleles in the genomic DNA can be sequenced.

In some embodiments, the target polynucleotide region contains a single nucleotide polymorphism (SNP), an insertion or deletion, or a copy number variation. The target polynucleotide region may be a loci or allele. For example, the alleles or loci may contain a drug metabolizing enzyme and transporter gene.

In one embodiment, the methods of the present invention provide for selecting a subset of SNPs located to a region of interest. In one aspect, methods of the present invention can be used to sequence an entire genome, part of a genome, one chromosome, or part of a chromosome, permitting chromosome specific sequencing. 1, 2, 3, 4 or more capture probes may be used to capture all possible alleles at known loci.

In some embodiments, the methods of the present invention comprise the steps of: a) immobilizing a set of loci-specific probes (also referred to as "capture probes") on a substrate, wherein the probes have defined sequences; b) hybridizing a sample containing a target polynucleotide to the set of loci-specific probes; c) ligating a first solution probe to the loci-specific probe, wherein the solution probe carries a cleavage site (near the 3'end) and hybridizes to the target polynucleotide; d) providing a nucleotide reversible terminator to the hybridization duplexes resulted from steps b) and c), wherein the nucleotide reversible terminator prevents base extension of complexes formed by nonspecific hybridization; e) cleaving the nucleotide reversible terminator at the cleavage site present on the first solution probe; and f) placing the target-probe hybridization duplexes under nucleic acid synthesis conditions in the presence of free nucleotides to allow extension of the probe that is complementary to the target polynucleotide. In some embodiments, the method further comprises obtaining sequence information of the target polynucleotide via a computer system. In some embodiments, the target polynucleotide is genomic DNA. In some embodiments, the first solution probe is labeled and have at least one base that is degenerate. In one embodiment, the first solution probe is a 9-mer, i.e. contains 9 nucleotides. The subject method provides higher hybridization specificity of at least 95%, 96%, 97%, 98%, 99%, 99.5% or more. In some embodiments, the loci-specific first solution probes and/or capture probes are allele-specific. In some embodiments, 1, 2, 3, 4 or more different solution probes are used.

In some embodiments, the methods of the present invention comprise the steps of: a) immobilizing a set of loci-specific probes on a substrate, wherein the probes have defined sequences; b) hybridizing a sample containing a target polynucleotide to the set of loci-specific probes which bind to loci sites; c) ligating a first solution probe (5'phosphate) to the first loci-specific probe, wherein the solution probe carries a cleavage site (near 3'end) and hybridizes to the target polynucleotide; d) providing a nucleotide reversible terminator to the hybridization duplexes resulted from steps b) and c), wherein the capping step blocks base extension; e) cleaving the nucleotide reversible terminator at the cleavage site present on the solution probe to allow base extension; f) ligating a second solution probe to the first solution probe such that the second solution probe hybridizes to the target polynucleotide; g) washing the hybridization duplexes from step f) to remove nonspecific hybridization between the second solution probe and the target polynucleotide; h) ligating a third set of solution probes carrying a common primer at 3' end to the previously ligated solution probe such that the solution probe carrying the primer hybridizes to the target polynucleotide; i) washing the hybridization duplexes from step h) to remove the target polynucleotide from the hybridization duplexes; j) adding primers that are complementary to the common primer at 3' end of the solution probes to allow primer annealing; and k) placing the single strand probe polynucleotide under nucleic acid synthesis conditions in the presence of free nucleotides to allow base extension from the annealed primer at the 3' end based on nucleic acid sequence of the probe strand that is complementary to the target polynucleotide. In some embodiments, the method further comprises obtaining sequence information of the target polynucleotide via a computer system. In some embodiments, the target polynucleotide is genomic DNA. In some embodiments, the solution probes are labeled and have at least one base that is degenerate. In one embodiment, the solution probe is a 9-mer, i.e. contains 9 nucleotides. In some embodiments, the washing condition is sufficiently stringent such that the solution probes that have nonspecifically hybridized to the target polynucleotide can be washed off. In other embodiments, the washing condition is sufficiently stringent such that the target polynucleotide can be washed off from the hybridization duplex. The cycle of ligation between the solution probe and the target polynucleotide followed by stringent washing to remove nonspecific ligation can be repeated more than one time. The subject ligation-captured sequencing method provides higher hybridization specificity. The specificity can be at least 95%, 96%, 97%, 98%, 99%, 99.5% or more. In some embodiments, the loci-specific probes or capture probes are allele-specific.

I. Ligation Assisted Sequencing

One aspect of the present invention relates to a method for determining or identifying nucleotide sequence via ligation assisted sequencing. This method generally comprises hybridization between an allele-specific, sequence-defined probe and a target polynucleotide, ligation between a first solution probe comprising a cleavable cap and the target polynucleotide, capping of the 3' end of capture probes not ligated to the first solution probe, removing the 3' end cap on the first solution probe to prevent blocking of base extension of the specific hybridization product, and enzymatic reaction to allow base extension complementary to the target polynucleotide by for example, polymerase chain reaction.

Target Preparation

In one aspect, the present invention provides a method for sequencing a genome or at least 50%, 85%, 95% or 99% of the genome. In some embodiments, the target polynucleotide is genomic DNA or a part of the genomic DNA. While some embodiments are for sequencing whole genome at more than 50% coverage, these embodiments and some other embodiments are also suitable for sequencing a targeted region such as genomic regions relating to drug metabolism. In one example, the target polynucleotide is human genomic DNA. The subject methods can sequence at least 50%, 85%, 90%, 95%, 96%, 97%, 98%, 99%, 99.1%, 99.2%, 99.3%, 99.4%, 99.5%, 99.6%, 99.7%, 99.8%, 99.9% or more of the genome, for example, human genome. The number of probes used for sequencing a genome using the subject methods of the present invention is fewer as compared to other genome sequencing techniques currently available. In some embodiments, no more than 200 million probes are used. For example, 200 million probes can be used to sequence at least 95% of the human genome. In some embodiments, the probes are loci- and/or allele-specific. In some embodiments, the sequences of the probes are known or defined. The design of the probes of the present invention is described herein below.

"Nucleic acid" or "oligonucleotide" or "polynucleotide" or grammatical equivalents typically refer to at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-0 atom with the 4'-C atom, All of these references are hereby expressly incorporated by reference. These modifications of the ribose-phosphate backbone may be done to increase the stability and half-life of such molecules in physiological environments. For example, PNA:DNA and LNA-DNA hybrids can exhibit higher stability and thus may be used in some embodiments. The target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The term "target polynucleotide" typically refers to a nucleic acid of interest. In one aspect, target nucleic acids of the invention are genomic nucleic acids. DNA derived from the genetic material in the chromosomes of a particular organism is genomic DNA. A genomic library is a collection of clones made from a set of randomly generated overlapping DNA fragments representing the entire genome of an organism. Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification, isolated by amplification using methods known in the art, including without limitation polymerase chain reaction (PCR), whole genome amplification (WGA), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes.

In some embodiments, the methods of the present invention involve no amplification of the target polynucleotide, for example, genomic DNA. In this case, a few micrograms of genomic DNA will have about million copies of genomic DNA per microliter.

In some embodiments, the methods of the present invention comprise capture of target polynucleotide. The target polynucleotide may be from a known region of the genome. In one embodiment, oligo probes can be immobilized on beads and these oligo beads which are inexpensive and reusable can be used to capture the target genomic polynucleotide. In another embodiment, Nimblegen microarrays are used to capture target polynucleotide. NimbleGen arrays are particularly suited for chromatin immunoprecipitation-microarray hybridizations (ChIP-chip) which use whole genome arrays, whole genome promoter specific arrays, or custom designed arrays; and comparative genomic hybridization (CGH) which uses whole human genome tiled arrays or custom designed region specific arrays. In another embodiment, Agilent RNA oligos can be used to capture target polynucleotide of the present invention.

In some embodiments, target polynucleotide is amplified using standard amplification methods known in the relevant art. In one embodiment, the target polynucleotide is prepared by whole genome amplification (WGA). The most recently developed WGA methods include the ligation-mediated PCR (LMP), the T7-based linear amplification of DNA (TLAD) and the multiple displacement amplification (MDA). LMP is a method that uses endonuclease or chemical cleavage to fragment the gDNA sample and uses linkers and primers for its amplification. It was adapted for the WGA of small quantities of gDNA and single cells (Klein et al., 1999; Tanabe et al., 2003). Rubicon Genomics commercializes different kits (Omniplex) that allow for the amplification of RNA, DNA and methylated DNA sequences. The main advantages are that the method is able to amplify degraded DNA, and allows for different variations and that all steps are performed in the same tube. The main disadvantages are that it only amplifies a representation of the genome and it generates fragments only up to 2 kb. It has been reported to provide better CGH results than DOP-PCR (Pirker et al., 2004) but worse genotyping results than MDA (Bergen et al., 2005a). TLAD is a variant on the protocol originally designed by Phillips and Eberwine to amplify mRNA (Phillips and Eberwine, 1996) that has been adapted for WGA (Liu et al., 2003). It uses Alu I restriction endonuclease digestion and a terminal transferase to add a polyT tail on the 3' terminus. A primer is then used with a 5' T7 promoter and a 3' polyA tract, and Taq polymerase is used to synthesise the second strand. Then the sample is submitted to in vitro transcription reaction and posterior reverse transcription. The major advantage is that TLAD does not introduce sequence and length-dependent biases. Multiple displacement amplification (MDA) is a non-PCR-based isothermal method based on the annealing of random hexamers to denatured DNA, followed by strand-displacement synthesis at constant temperature (Blanco et al., 1989). It has been applied to small genomic DNA samples, leading to the synthesis of high molecular weight DNA with limited sequence representation bias (Lizardi et al., 1998; Dean et al., 2002). As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a proofreading activity resulting in error rates 100 times lower than the Taq polymerase (Eckert and Kunkel, 1991; Esteban et al., 1993). Recently, it has been shown that MDA, when used on genomic DNA sequences with high variability, results in a loss of heterozygosity (Murthy et al., 2005). The technology has been shown to be very sensitive and can amplify from single cells (Hellani et al., 2004, Handyside et al., 2005) and single bacteria (Raghunathan et al., 2005). Any of the herein disclosed method can be used in the methods of the present invention.

In another embodiment, the target polynucleotide is prepared by whole genome sampling assay (WGSA). The WGSA reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified. The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position. WGSA is disclosed in Kennedy et al. (2003), *Nat Biotechnol*, Vol., pp. 1233-1237, and U.S. patent application Ser. Nos. 09/920, 492, 09/904,039, 10/681,773, 10/316,517, 10/442,021, 10/463,991, 10/316,629, and 10/264,945 and U.S. Pat. No. 6,361,947, all of which are herein incorporated by reference. WGSA can simultaneously genotype more than 10,000 SNPs in parallel by allele-specific hybridization to perfect match (PM) and mismatch (MM) probes synthesized on an array. WGSA may not be able to assay the entire panels of loci.

In another embodiment, the target polynucleotide is prepared by long-range PCR. Long range PCR allows the amplification of PCR products, which are much larger than those achieved with conventional Taq polymerases. Up to 27 kb fragments are possible from good quality genomic DNA, although 10-20 kb fragments are routinely achievable, given the appropriate conditions. The method relies on a mixture of thermostable DNA polymerases, usually Taq DNA polymerase for high processivity (i.e. 5'-3' polymerase activity) and another DNA polymerase with 3'-5' proofreading abilities (usually Pwo). This combination of features allows longer primer extension than can be achieved with Taq alone. This method for detection of the FVIII gene intron 22 inversion (Liu et al, 1998) removes the requirement for Southern Blotting. Results can be obtained within 24 hours. Modifications from standard long range PCR protocols include the addition of DMSO and incorporation of deaza GTP to enable read through of a high GC content region upstream of the FVIII gene. The method relies on overlapping PCR to generate a constant band, which appears in all template DNA's. This band acts as a control to show that the reaction has worked efficiently. The largest amplification product seen using this method is 12 kb, well within the range of the enzyme mix utilized. Long-range PCR may be costly to assay singleton loci that are distant from groups of clustered loci.

In another embodiment, the target polynucleotide is prepared by locus-specific multiplex PCR. Multiplex locus specific amplification can be used to amplify a plurality of pre-selected target sequences from a complex background of nucleic acids. The targets are selected for amplification using splint oligonucleotides that are used to modify the ends of the fragments. The fragments have known end sequences and the splints are designed to be complementary to the ends. The splint can bring the ends of the fragment together and the ends are joined to form a circle. The splint can also be used to add a common priming site to the ends of the target fragments. Specific loci are amplified and can be subsequently analyzed. Locus-specific multiplex PCR can be very costly.

Other suitable amplification methods include but are not limited to the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603 each of which is incorporated herein by reference). Other amplification methods that may be used are described in, U.S. Pat. Nos. 5,242,794, 5,494, 810, 4,988,617 and in U.S. Ser. No. 09/854,317, each of which is incorporated herein by reference. Additional methods of sample preparation and techniques for reducing the complexity of a nucleic sample are described in Dong et al., Genome Research 11, 1418 (2001), in U.S. Pat. Nos. 6,361, 947, 6,391,592 and U.S. Ser. Nos. 09/916,135, 09/920,491, 09/910,292, and 10/013,598.

Naturally-existing targets can be assayed directly in cell lysates, in nucleic acid extracts, or after partial purification of fractions of nucleic acids so that they are enriched in targets of interest. In one example, the target polynucleotide is human genomic DNA. The polynucleotide target to be detected can be unmodified or modified. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, ether by chemical or enzymatic reaction such as ligation or polymerase-assisted extension. Alternatively, the internal labels and anchor ligands can be incorporated into an amplified target or its complement directly during enzymatic polymerization reactions using small amounts of modified NTPs as substrates.

The target polynucleotide can be isolated from a subject. The subject is not limited to a human being but may also be other organisms including but not limited to mammals, plants, bacteria, virus or fungi. In one example, the target polynucleotide is genomic DNA extracted from a human.

Methods of Laying Probes on Surface

In some embodiments, the methods of the invention comprise oligonucleotide probes, generally stretched on a substrate. The terms "substrate" or "solid support" or other grammatical equivalents as used herein typically refer to any material that is modified to allow "stretching" of nucleic acid molecules as described herein. In general, the substrate contains discrete individual sites (for example, nanochannels, flow cells, or lines) appropriate for the attachment or association of decorated nucleic acid molecules to form stretched nucleic acids and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresces.

Substrates of the invention can be configured to have any convenient geometry or combination of structural features. The substrates can be either rigid or flexible and can be either optically transparent or optically opaque, or have combinations of these surfaces. The substrates can also be electrical insulators, conductors or semiconductors. Further the substrates can be substantially impermeable to liquids, vapors and/or gases or, alternatively, the substrates can be substantially permeable to one or more of these classes of materials. In general, the substrates fall into two different classes: substrates comprising particular geometries such as nanochannels or nanopores, as more fully discussed below, or those that have surface characteristics to allow the stretching of decorated nucleic acids, such as the use of linear patterns of surface chemistries.

In one aspect of the invention, substrates of the invention comprise nanostructures or cells. Such structures can include without limitation nanopillars, nanopores and nanochannels. In many exemplary aspects, substrates of the invention comprise nanochannels. Such substrates are known in the art. For example, U.S. Pat. Nos. 7,217,562; 6,685,841; 6,518,189; 6,440,662; 6,214,246 describe nanostructures, including nanochannels, of use in accordance with the present invention. These patents are hereby incorporated by reference in their entirety. Generally, in these nanochannel substrates, there is a reservoir into which the oligonucleotide probes are placed, which are then moved into nanochannels, a single molecule of oligonucleotide probe per nanochannel, to form the stretched nucleic acids, followed by detection of the order, and optionally, the distance between the labels of the incorporated probes.

In some embodiments, the substrates comprise cells that are generally 1-2 millimeters thick. In one example, the substrate, e.g. a slide can be about 10 centimeters long. Another embodiment of nanostructures that finds use in the present invention are substrates comprising nanopores. Nanopore devices can provide single-molecule detection of molecules driven electrophoretically in solution through a nano-scale pore, and the sequence of nucleotides can be detected by the sequence of signals generated as each nucleotide passes through the pore. Such nanopores and methods of sequencing using nanopores are known in the art and discussed in for example, Branton et al., (2008), Nature, 26(10):1 146-53 and in U.S. Pat. Nos. 6,673,615; 7,258,838; 7,238,485; 7,189,503; 6,627,067; 6,464,842; 6,267,872 and U.S. Patent Application Nos. 20080248561; 20080171316, 20080102504, each of which is herein incorporated by reference in its entirety for all purposes, and in particular for the figures, legends and accompanying text describing the compositions, methods of using the compositions and methods of making the compositions.

In some embodiments, the oligonucleotide probe is immobilized on a solid support before binding to the target polynucleotide. In one embodiment, the 5' end of an oligonucleotide probe of the present invention is attached to a solid surface or substrate. Oligonucleotide can be immobilized by various methods known in the art including, (without limitation) covalent cross-linking to a surface (e.g., photochemically or chemically), non-covalent attachment to the surface through the interaction of an anchor ligand with a corresponding receptor protein (e.g. biotin-streptavidin or digoxigenin-anti-digoxigenin antibody), or through hybridization to an anchor nucleic acid or nucleic acid analog. The anchor nucleic acid or nucleic acid analog have sufficient complementarity to the target (i.e., their formed duplex has sufficiently high Tm) that the anchor-target-probe complex will survive stringent washing to remove unbound targets and probes, but they do not overlap with the target site that is complementary to the probe antisense sequence.

The solid substrate can be made of any material to which the molecules can be bound, either directly or indirectly. Examples of suitable solid substrates include flat glass, quartz, silicon wafers, mica, ceramics and organic polymers such as plastics, including polystyrene and polymethacrylate. The surface can be configured to act as an electrode or a thermally conductive substrate (which enhances the hybridization or discrimination process). For example, micro and sub-micro electrodes can be formed on the surface of a suitable substrate using lithographic techniques. Smaller nanoelectrodes can be made by electron beam writing/lithography. Electrodes can also be made using conducting polymers which can be pattern a substrate by ink jet printing devices by soft lithography or be applied homogenously by wet chemistry. $TnO_2$ coated glass substrates are available. Electrodes can be provided at a density such that each immobilized molecule has its own electrode or at a higher density such that groups of molecules or elements are connected to an individual electrode. Alternatively, one electrode may be provided as a layer below the surface of the array which forms a single electrode. The solid substrate may optionally be interfaced with a permeation layer or a buffer layer. It is also possible to use semi-permeable membranes such as nitrocellulose or nylon membranes, which are widely available. The semi-permeable membranes can be mounted on a more robust solid surface such as glass. The surface layer may comprise a sol-gel. The surfaces may optionally be coated with a layer of metal, such as gold, platinum or other transition metal. A particular example of a suitable solid substrate is the commercially available SPR BIACore™ chip (Pharmacia Biosensors). Heaton et al., 2001 (PNAS 98:3701-3704) have applied an electrostatic field to an SPR surface and used the electric field to control hybridization.

The solid substrate is generally a material having a rigid or semi-rigid surface. In some embodiments, at least one surface of the substrate is substantially flat, although in some embodiments it may be desirable to physically separate discrete elements with, for example, raised regions or etched trenches. For example, the solid substrate may comprise nanovials—small cavities in a flat surface e.g. 10 µm in diameter and 10 µm deep. This is particularly useful for cleaving molecules from a surface and performing assays or other processes such as amplification in them. The solution phase reaction is more efficient than the solid phase reaction, whilst the results remains spatially addressable, which is advantageous. Other formats include but are not limited to synthetic or natural beads, membranes or filters, slides including microarray slides, microtiter plates, microcapillaries, and microcentrifuge tubes.

In some embodiments, the loci-specific oligo probes are coated or attached onto beads for capturing genomic DNA. The oligo probes can be directed against large regions on genomic DNA that include multiple loci of interest. For example, many ADME (absorption, distribution, metabolism, and excretion) markers are on about 200 genes. Hybridization between loci-specific oligo probes and target polynucleotide can be carried out on beads in columns at a controlled temperature and salt concentration. The hybridization products can be eluted from the beads with moderate pressure.

The use of a solid support with an array of capture oligonucleotides is fully disclosed in U.S. Patent Application Ser. No. 60/011,359, which is hereby incorporated by reference. When using such arrays, the oligonucleotide primers or probes used in the above-described coupled PCR and LDR phases, respectively, have an addressable array-specific portion. After the LDR or PCR phases are completed, the addressable array-specific portions for the products of such processes remain single stranded and are caused to hybridize to the capture oligonucleotides during a capture phase. C. Newton, et al., "The Production of PCR Products With 5' Single-Stranded Tails Using Primers That Incorporate Novel Phosphoramidite Intermediates," Nucl. Acids Res. 21(5): 1155-62 (1993), which is herein incorporated by reference.

During the capture phase of the process, the mixture can be contacted with the solid support at a temperature of 45-90° C. and for a time period of up to 60 minutes. Hybridizations may be accelerated by adding cations, volume exclusion or chaotropic agents. When an array consists of dozens to hundreds of addresses, it is important that the correct ligation product sequences have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

Loading of nucleic acids onto these substrates can be modulated and/or controlled by the flow and/or electrical forces, including diffusion forces and surface forces exerted by areas of differential charge and/or hydrophobicity. The number of nucleic acids applied to the substrate (i.e., with a loading buffer or other solution) can be adjusted to assure maximal occupancy of the linear features with non-overlapping nucleic acid molecules and thus minimize the number of empty linear features on the substrate. In an exemplary embodiment, at least 50% of the linear features of a substrate are occupied by at least one nucleic acid molecule. In a further embodiment, at least 60%, 70%, 80%, 90%, and 95% of the linear features are occupied by one or more nucleic acids.

Two exemplary approaches of laying probes are disclosed herein below for illustrative purposes. The first approach is "In Situ" oligonucleotide synthesis in which the probes are in known geographic locations in the X-Y coordinate plane. In one embodiment, the oligonucleotide probe is synthesized on the surface. Examples of technologies that allow on-surface oligo synthesis include but are not limited to photolithography and ink jet. In another embodiment, the pre-synthesized oligonucleotide probes are spotted onto the surface. Various microarray protocols, for example, protocol for Agilent inkjet-deposited pre-synthesized oligo arrays are known to one skilled in the art.

Polymers such as nucleic acids or polypeptides can be synthesized in situ using photolithography and other masking techniques whereby molecules are synthesized in a step-wise manner with incorporation of monomers at particular positions being controlled by means of masking techniques and photolabile reactants. For example, U.S. Pat. No. 5,837,832 describes a method for producing DNA arrays immobilized to silicon substrates based on very large scale integration technology. In particular, U.S. Pat. No. 5,837,832 describes a strategy called "tiling" to synthesize specific sets of probes at spatially-defined locations on a substrate. U.S. Pat. No. 5,837,832 also provides references for earlier techniques that can also be used. Light directed synthesis can also be carried out by using a Digital Light Micromirror chip (Texas Instruments) as described (Singh-Gasson et al., (1999) Nature Biotechnology 17:974-978). Instead of using photo-deprotecting groups which are directly processed by light, conventional deptotecting groups such as dimethoxy trityl can be employed with light directed methods where for example a photoacid is generated in a spatially addressable way which selectively deprotects the DNA monomers (McGall et al PNAS 1996 93: 1355-13560; Gao et al J. Am. Chem Soc. 1998 120: 12698-12699). Electrochemical generation of acid is another means that can be used in the subject methods of the present invention.

The "in situ" arrays can have about 1,000 to 100,000,000 array probes (features). In one embodiment, the "in situ" array carries approximately 200,000,000 probes.

The second approach of laying probes on a surface is "Lawn" approach in which a finite set of probes, for example, pre-synthesized oligos, are laid down randomly at controlled density on a surface or flow cell. In this case, single probe molecules should be sufficiently separated to allow detection of independent events. In some embodiments, the "lawn" surface has at least one hundred of independent redundant reads off each unique probe sequence. In some embodiments, Helicos molecular barcoding techniques and single molecule sequencing can be used in the subject methods (Pushkarev D, Neff N F, Quake S R. Nat Biotechnol. August 2009). The HeliScope™ Single Molecule Sequencer is a genetic analyzer for direct DNA measurement utilizing Helicos True Single Molecule Sequencing (tSMS)™ technology. As a DNA microscope, the HeliScope instrument performs tSMS chemistry and captures images to observe sequencing-by-synthesis reactions for billions of individual DNA molecules in parallel. Multiplexed barcoded samples run on the HeliScope™ Single Molecule Sequencer saves money and boosts research productivity by increasing the number of analyzable samples per run. In some embodiments, barcoding used in the subject methods allows loading of 5 identifiable individual samples per channel on a 50-channel flow cell. In one embodiment, it allows 250 individuals, i.e. barcoded DNA samples to be analyzed per flow cell. One can sequence 2.5 megabases from five different samples per channel at 15× coverage for less than $72 per sample. Samples can be prepared simply without amplification. Oligonucleotides can be ligated to the DNA in the samples followed by barcode reading.

Molecules that can be immobilized in the array include nucleic acids such as DNA and analogues and derivatives thereof, such as PNA. Nucleic acids can be obtained from any source, for example genomic DNA or cDNA or synthesized using known techniques such as step-wise synthesis. Nucleic acids can be single or double stranded. DNA nanostructures or other supramolecular structures can also be immobilized. Other molecules include but are not limited to compounds joined by amide linkages such as peptides, oligopeptides, polypeptides, proteins or complexes containing the same; defined chemical entities, such as organic molecules; conjugated polymers and carbohydrates or combinatorial libraries thereof.

Molecules can be labeled to enable interrogation using various methods. Suitable labels include: optically active dyes, such as fluorescent dyes; nanoparticles such as fluorospheres and quantum dots, rods or nanobars; and surface plasmon resonant particles (PRPs) or resonance light scattering particles (RLSs)—particles of silver or gold that scatter light (the size and shape of PRP/RLS particles determines the wavelength of scattered light). See Schultz et al., 2000, PNAS 97: 996-1001; Yguerabide, J. and Yguerabide E., 1998, Anal Biochem 262: 137-156.

Probe Design

In some embodiments of the hybridization phase, a loci-specific oligonucleotide probe is provided ("capture probe"). The nucleotide sequence of the probe is known. In some embodiments, the probe is specific to a locus of interest. The loci of interest include but are not limited to single nucleotide polymorphism (SNP), adjacent SNPs, insertion or deletions, for example, up to 10 base-pair (bp), and copy number variation (CNV), for example, integer copy calls.

In some embodiments, the locus of interest is a SNP including tri-allelic and quad-allelic. A single-nucleotide polymorphism (SNP) is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case there are two alleles: C and T. Within a population, SNPs can be assigned a minor allele frequency—the lowest allele frequency at a locus that is observed in a particular population. This is simply the lesser of the two allele frequencies for single-nucleotide polymorphisms. There are variations between human populations, so a SNP allele that is common in one geographical or ethnic group may be much rarer in another.

Single nucleotide may be changed (substitution), removed (deletions) or added (insertion) to polynucleotide sequence. Ins/del SNP may shift translational frame. Single-nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed synonymous—if a different polypeptide sequence is produced they are nonsynonymous. A nonsynonymous change may either be missense or nonsense, where a missense change results in a different amino acid, while a nonsense change results in a premature stop codon. SNPs that are not in protein-coding regions may still have consequences for gene splicing, transcription factor binding, or the sequence of non-coding RNA.

Variations in the DNA sequences of humans can affect how humans develop diseases and respond to pathogens, chemicals, drugs, vaccines, and other agents. SNPs are also thought to be key enablers in realizing the concept of personalized medicine. Another great importance of SNPs in biomedical research is for comparing regions of the genome between cohorts (such as with matched cohorts with and without a disease). The study of single-nucleotide polymorphisms is also important in crop and livestock breeding programs (genotyping). In one aspect, the present invention provides methods used to identify SNPs.

In some embodiments, the loci of interest include CNVs. A copy number variation (CNV) is a segment of DNA in which copy-number differences have been found by comparison of two or more genomes. The segment may range from one kilobase to several megabases in size. Humans (being diploid) ordinarily have two copies of each autosomal region, one per chromosome. This may vary for particular genetic regions due to deletion or duplication. CNVs may either be inherited or caused by de novo mutation. A recently proposed mechanism for the cause of some CNVs is fork stalling and template switching, a replication misstep. Therefore, CNVs can be caused by genomic rearrangements such as deletions, duplications, inversions, and translocations. Low copy repeats (LCRs) which are region specific repeat sequences are susceptible to such genomic rearrangements resulting in CNVs. Factors such as size, orientation, percentage similarity and the distance between the copies renders them susceptible (Lee J A, Carvalho C M, Lupski J R. (2007) *Cell* 131 (7): 1235-47; Lee J. A., Lupski J. R. (2006) Neuron, 52 (1), pp. 103-121).

Copy number variation can be discovered by cytogenetic techniques such as fluorescent in situ hybridization, comparative genomic hybridization, array comparative genomic hybridization, and by virtual karyotyping with SNP arrays.

In one embodiment, the present invention provides methods for identifying and sequencing CNVs. It is estimated that approximately 0.4% of the genomes of unrelated people typically differ with respect to copy number (Kidd J M, Cooper G M, Donahue W F, et al. (May 2008). *Nature* 453 (7191): 56-64). Like other types of genetic variation, some CNVs have been associated with susceptibility or resistance to disease. Gene copy number can be elevated in cancer cells. For instance, the EGFR copy number can be higher than normal in non-small cell lung cancer (Cappuzzo F, Hirsch, et al. (2005 *Journal of the National Cancer Institute* 97: 643-655). In addition, a higher copy number of CCL3L1 has been associated with lower susceptibility to human HIV infection (Gonzalez, E. et al. (2005). *Science* 307: 1434-1440), and a low copy number of FCGR3B (the CD16 cell surface immunoglobulin receptor) can increase susceptibility to systemic lupus erythematosus and similar inflammatory autoimmune disorders (Aitman T. J. et al. (2006). *Nature* 439: 851-855). Copy number variation has also been associated with autism, schizophrenia, and idiopathic learning disability (Cook E H, Scherer S W (2008). *Nature* 455 (7215): 919-23). In humans, CNVs encompass more DNA than SNPs. CNVs can be limited to a single gene or include a contiguous set of genes. CNVs can result in having either too many or too few of the dosage sensitive genes, which may be responsible for a substantial amount of human phenotypic variability, complex behavioral traits and disease susceptibility. In certain cases, such as rapidly growing Escherichia coli cells, the gene copy number can be 4-fold greater for genes located near the origin of DNA replication, rather than at the terminus of DNA replication. Elevating the gene copy number of a particular gene can increase the expression of the protein that it encodes.

In some embodiments, the methods of the present invention can be used to sequence a panel of loci. In one aspect, a panel of alleles may be sequenced. For example, the loci of interest include drug metabolizing enzyme and transporter (DMET). A common genomic technique is drug metabolizing enzyme and transporter (DMET) analysis, which is used to identify a subjects' likely response to a drug candidate based on the type and number of each of the two molecules that he or she produces. Many drug developers use DMET as part of wider absorption, distribution, metabolism, and elimination (ADME) analysis to identify patients who are most likely to derive benefits from a developmental treatment. The methods of the present invention may allow screening of about 2,000 drug metabolism markers across about 200 genes simultaneously. In other embodiments, the methods of the present invention can be used in advancing genome-wide association studies (GWAS) to identify common genetic factors that influence health and disease and sequence hundreds of high-value markers based on diseases.

In some embodiments, the loci-specific probes of the present invention are high fidelity oligonucleotide probes. The loci-specific probe set of the present invention may have very low proportion of incomplete and incorrect probes. In some embodiments, the loci-specific probe contains at least 10 nucleotides, for example, 50 nucleotides, i.e. 50-mer. The oligonucleotide probes of the present invention can range from 10 to 10,000 nucleotides (nt) in length, for example, from 50 to 2000 nt in length, including from 50-500 nt. The loci-specific probe can be 10, 15, 20, 25, 30, 35, 40, 45, 50, 55, 60, 65, 70, 80, 90, 100, 110, 120, 130, 140, 150 nucleotides or longer. In one example, the loci-specific probe is a 50-mer. In some embodiments, the loci-specific probe is immobilized on a surface or a flow cell at its 5' end and the probe is extendable at the 3' hydroxy (OH) end. In one aspect, the loci-specific probes are allele-specific.

Figure 3:
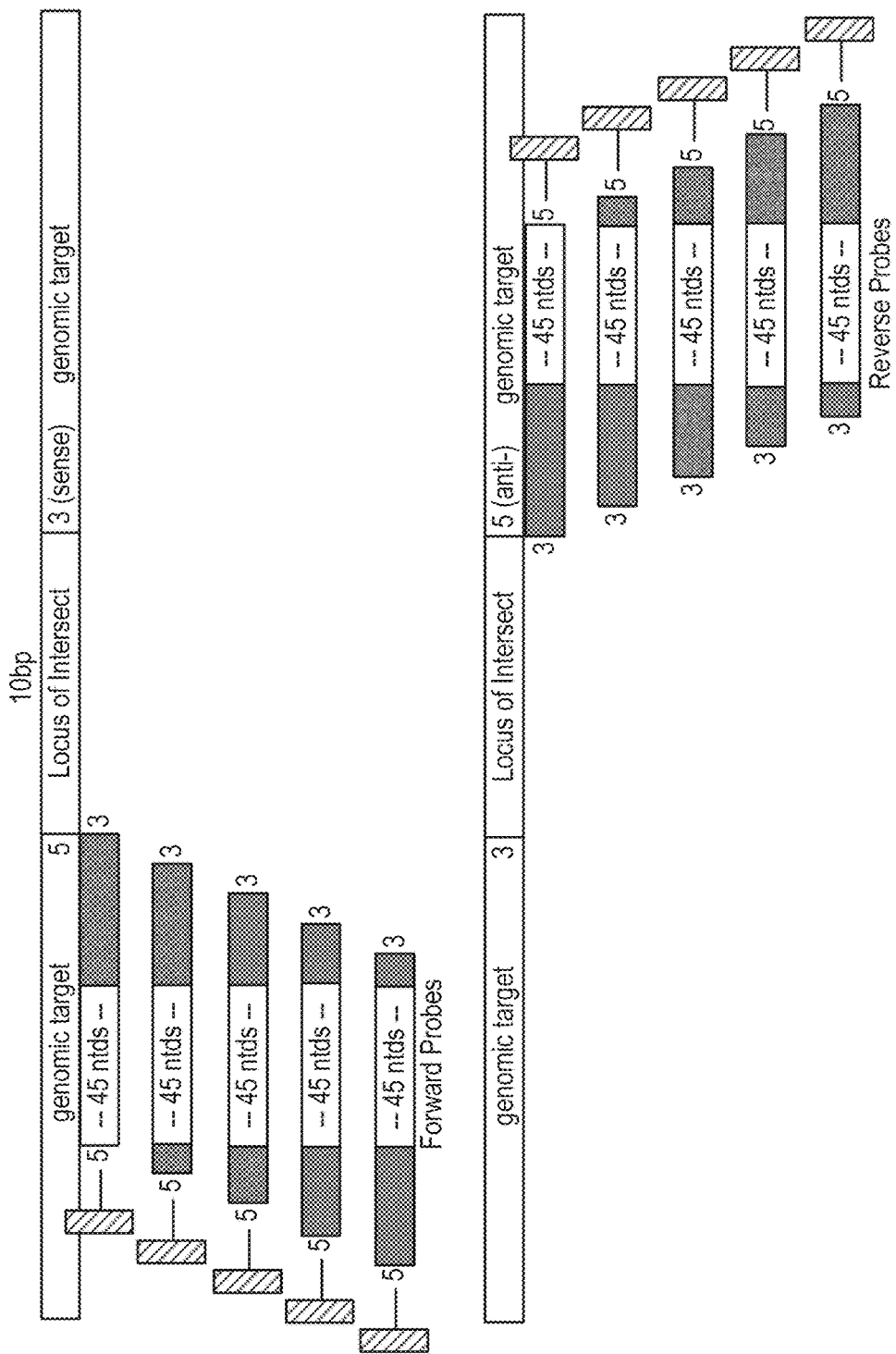
FIG. 3 shows an example of probe design for targeted sequencing. The figure shows a 10 bp locus of interest within genome 50-mer probes immobilized on surface at 5' end with forward and reverse orientation probes.
Figure 4:
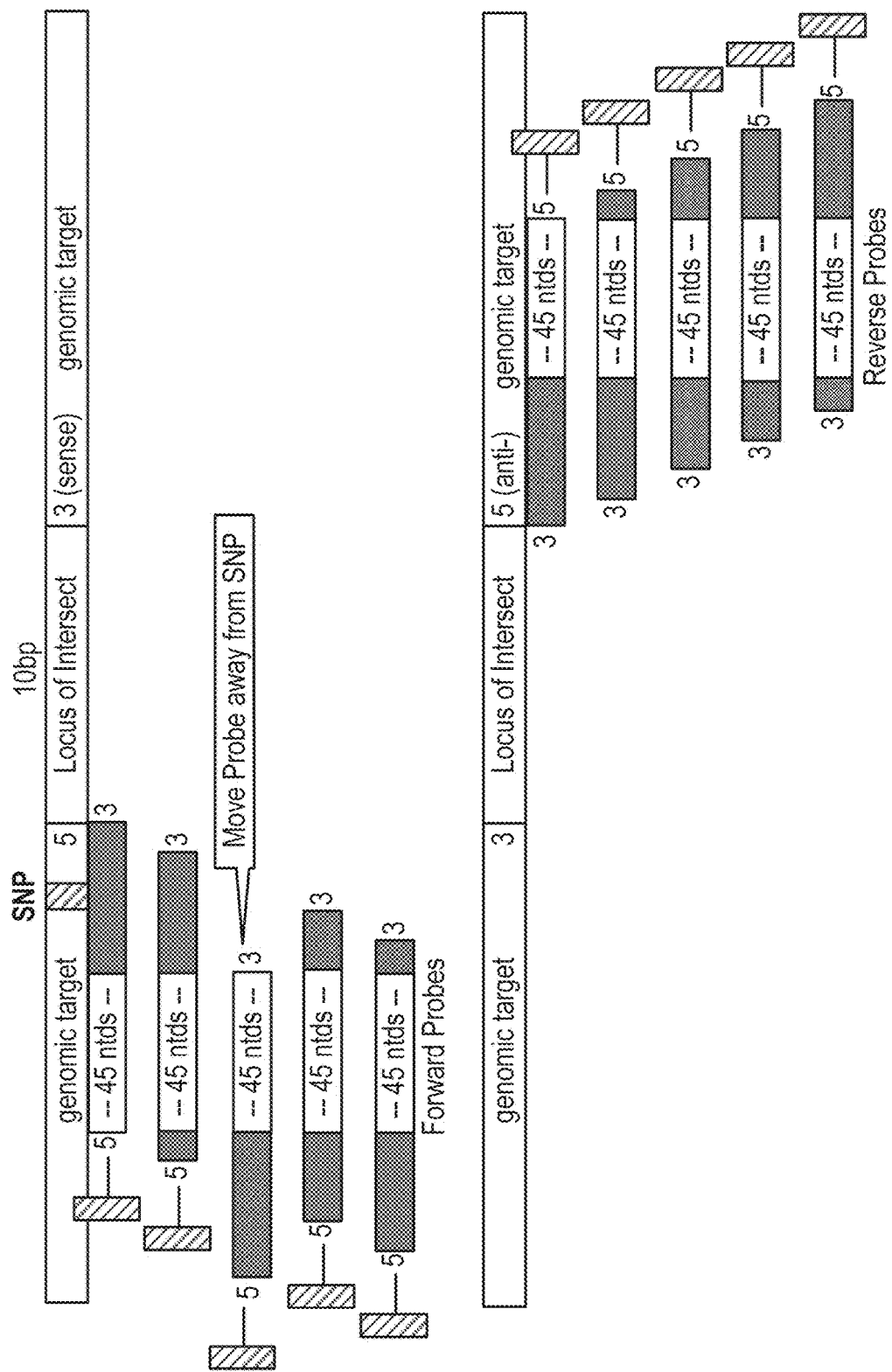
FIG. 4 shows an example of probe design for targeted sequencing. The probe should avoid HapMap single-nucleotide polymorphism (SNP) with MAP>0.05 at 3' end of probe sequences.
Figure 5A:
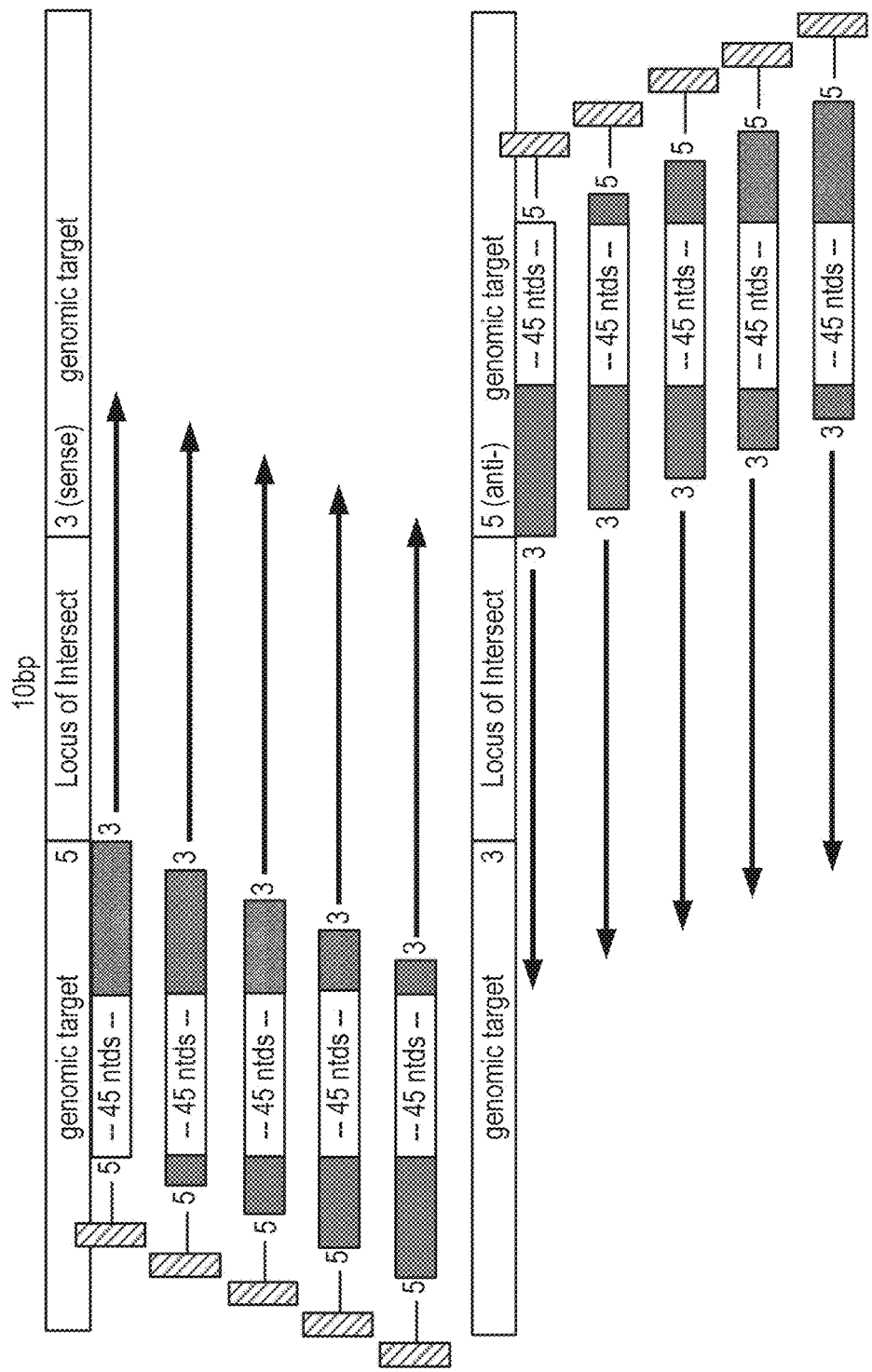
FIG. 5A, B shows an example of probe design for targeted sequencing (FIG. 5A) and expected distribution (FIG. 5B) of read depth. Arrows represent sequence reads.
Figure 5B:
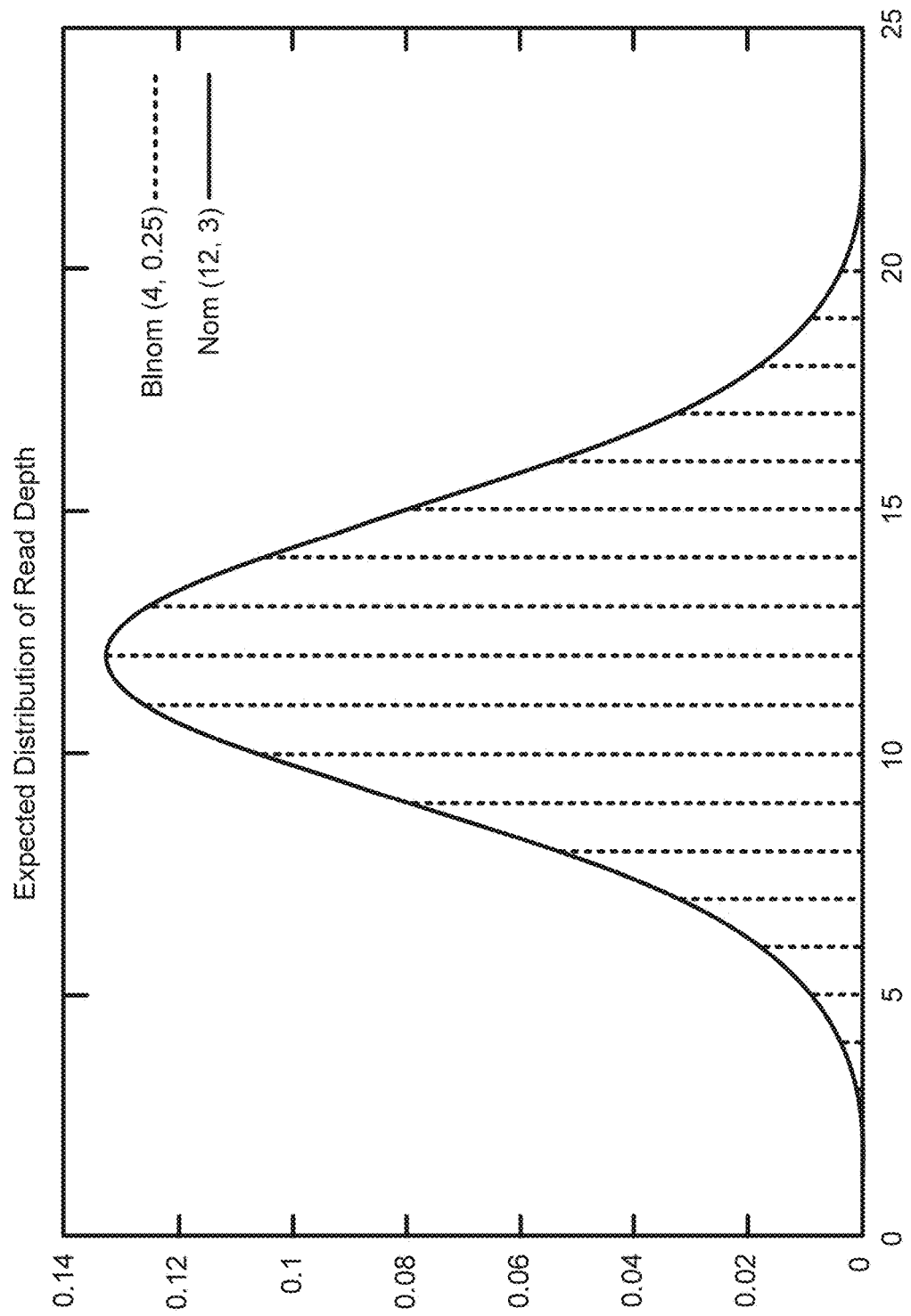

In one embodiment, assuming a locus or allele of interest is about 10 by long. There can be 10 unique probe sequences per locus, in which 5 staggered probes are offset by one base. The probes can be in both forward and reverse orientations. An exemplary design of 10-bp locus of interest within genome 50-mer probes immobilized on surface at 5' end is shown in FIG. 3. In some embodiments, the probes are designed to avoid SNPs with respect to minor allele frequency cutoff values of >0.05 at extreme 3' end of the probe sequences (FIG. 4). HapMap allele frequencies can be used. Exemplary sequence reads of about 15 bases or more and the expected distribution of read depth are shown in FIG. 5.

In some embodiments, "in situ" array features will each have at least hundreds of unique probe molecules with targets after hybridization and highly stringent washing. In some embodiments, at least two loci-specific or allele specific oligo probes are used to probe the same region on a target polynucleotide. The loci- or allele-specific or probes can be offset by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases or more to cover a certain region of the target polynucleotide, for example, genomic DNA.

In some embodiments, the present invention provides a method of performing a genomic sequencing reaction. Since the sequences of the probes are loci-specific and known, the number of duplicate probes for sequencing a certain region of the genome can be reduced. In one embodiment, there is no duplicate probe used in the subject methods. In another embodiment, 1, 2, 3, 4, or 5 duplicate probes are used.

FIG. 8A-C shows probe design sequences for five example loci from the PharmaADME panel (PharmaADME.org). Each locus is represented by sets of five overlapping probe sequences in both the forward and reverse orientations. The five loci include examples of a deletion, insertion, copy number, and two SNP variants (FIG. 8A). The probe sequences for the copy number example at CYP2A6 were modified from a primer sequence described in Fukami et al 2006 (*Pharmacogenomics Journal* 6: 401-412). FIG. 8B discloses "Forward_Probes" as SEQ ID NOS 7-31 and FIG. 8C discloses "Reverse_Probes" as SEQ ID NOS 32-56, all respectively, in order of appearance.

The loci-specific probes of the present invention may offer several advantages. Ordinary short oligonucleotide probes usually provide higher sequence-specificity but lower efficacy of hybridization than longer ordinary oligonucleotide probes where both are fully complementary to the target polynucleotide. The loci-specific, sequence-known oligonucleotide probes according to the present invention combine the hybridization efficacy of long probes with the sequence-specificity of short probes. In some embodiments, these loci-specific, sequence-known probes provide higher affinities toward their polynucleotide targets than short hybridization probes as well as increased sensitivity (signal-to-noise ratio) for target detection in comparison to ordinary long hybridization probes, which themselves are more sensitive than the shorter probes. In some embodiments, more than one probe that is specific for a region of the target polynucleotide is used. The probe is suitable for hybridization on complementary strands of a corresponding target nucleotide sequence to permit formation of a polymerase chain reaction product. In certain embodiments, an oligonucleotide probe according to the invention contains a single polynucleotide sequence, while in other embodiments, an oligonucleotide probe contains multiple polynucleotide sequences (so called bi-partite, tri-partite, tetra-partite, etc.). Oligonucleotide probes according to the present invention can include virtually any kind of nucleotide base, including (but not limited to) unmodified RNA bases, unmodified DNA bases or both (e.g., RNA-DNA chimeric polynucleotides) as well as one or more chemically modified RNA or DNA residue. Depending on their length and the presence of modified residues, the probes can be either chemically synthesized or prepared by enzymatic polymerization using techniques known in the art. In addition to ordinary RNA and DNA polymerases, mutated or engineered versions of polymerase enzymes can be used to incorporate into the probes variety of modified nucleotides.

The loci- and allele-specific oligonucleotide probes described herein can substitute for ordinary probes in commonly used hybridization methods such as dot/slot blots, Northern and Southern blots, in situ hybridization, sandwich hybridization, and gel-shift assays. These probes allow faster, more accurate and more sensitive detection and quantification of target polynucleotides with a higher level of multiplexing than ordinary hybridization probe.

In certain embodiments, the loci- and allele-specific oligonucleotide probes of the present invention can be modified to include additional functional moieties (also called modified oligonucleotide probes). Exemplary functional moieties include, without limitation, radioactive and fluorescent labels as well as anchor ligands such as biotin or digoxigenin. The functional moieties can be located internally or at either end of the probes. Probe modification can be carried out post-synthetically by chemical or enzymatic reactions such as ligation or polymerase-assisted extension. Alternatively, internal labels and anchor ligands can be incorporated into probes directly during enzymatic polymerization reactions using trace amounts of modified NTPs as substrates.

The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof.

Hybridization

In one aspect, the present invention provides a method for sequencing a target polynucleotide comprising the steps of: a) hybridizing a target polynucleotide to an allele-specific and sequence-defined capture probe; b) adding a first solution probe and ligase to the target-probe hybridization complexes to allow ligation of the solution probe to the substrate-attached probe and hybridization between the first solution probe and the target polynucleotide; c) capping the 3' end of the target-probe hybridization duplexes with a nucleotide reversible terminator; d) cleaving the 3' cap on the specific target-probe hybridization duplexes at the cleavage site present on the first solution probe; and (e) placing the specific target-probe hybridization duplexes under nucleic acid synthesis conditions in the presence of labeled nucleotides to allow extension of the probe that is complementary to the target polynucleotide.

In another aspect, the method further comprises the steps of: f) ligating a second solution probe to the first solution probe such that the second solution probe hybridizes to the target polynucleotide; g) washing the hybridization duplexes from step f) to remove nonspecific hybridization between the second solution probe and the target polynucleotide; h) ligating a set of third solution probes carrying a common primer at 3' end to the previously ligated solution probe such that the solution probe carrying the primer hybridizes to the target polynucleotide; i) washing the hybridization duplexes from step h) to remove the target polynucleotide from the hybridization duplexes; j) adding primers that are complementary to the common primer at 3' end of the third solution probes to allow primer annealing; and k) placing the single strand probe polynucleotide under nucleic acid synthesis conditions in the presence of free nucleotides to allow base extension from the annealed primer at the 3' end based on nucleic acid sequence of the probe strand that is complementary to the target polynucleotide. The methods of the present invention further comprise obtaining sequence information of the target polynucleotide via a computer, e.g. a computer software or algorithm.

"Hybridization" as used herein typically refers to the technique of allowing two single-stranded polynucleotide sequences with some degree of complementarity to bind to one another to form a stable double-stranded polynucleotide. "Complementary" and its equivalents as used herein generally refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 70% of the nucleotides of the other strand, usually at least about 80%, 85%, 90% to 95%, and more preferably from about 98 to 100%. See, M. Kanehisa Nucleic Acids Res. 12:203 (1984), incorporated herein by reference.

Hybridization usually involves the steps of 1) allowing binding between probe and target; and 2) washing away unbound or weakly bound probes under stringent conditions, wherein stringent hybridization conditions are those washing conditions that provide dissociation for imperfect complexes while preserving the intended complexes between target-specific probes and corresponding targets. Improvements in hybridization characteristics can be improvements in the selectivity of hybridization (sequence specificity and mismatch discrimination), the sensitivity of hybridization (ratio of absolute signal to background signal, signal-to-noise ratio), the affinity between probe and target (ratio of binding rate to dissociation rate between hybridization probes and targets); the stability of the duplex or complex (thermal stability, Tm; also kinetic inertness of dissociation or kinetic trap), or the efficiency or efficacy of hybridization (hybridization rate and/or yield of complex between probe and target for a fixed time of incubation under hybridization conditions). Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual ($2^{nd}$ Ed. Cold Spring Harbor, N.Y, 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 all of which are incorporated herein by reference.

In some embodiments, the primary polymerase chain reaction mixture is subjected to two or more polymerase chain reaction cycles involving a denaturation treatment, a hybridization treatment, and an extension treatment. During hybridization, target-specific portions of the probe hybridize to the target nucleotide sequences. The extension treatment causes hybridized primary oligonucleotide primers to be extended to form primary extension products complementary to the target nucleotide sequence to which the primary oligonucleotide primers are hybridized.

One notable feature of the present invention is that the hybridization probe is allele-specific and the sequence of the probe is known so that the capture oligonucleotide probe can hybridize with the target polynucleotide sequence in a stable fashion. Unless the oligonucleotides are designed in this fashion, false positive signals may result due to capture of adjacent unreacted oligonucleotides from the same oligonucleotide set which are hybridized to the target. In one aspect, the ligation step with the solution probes and the subsequent capping of the 3' end of the hybridization products and the cleaving of the 3' end cap of the specific probe-target hybridization complexes allow for higher specificity of hybridization to be achieved. In some embodiments, the hybridization specificity is greater than 95%, 96%, 97%, 98%, 99%, 99.5% or higher.

N-mer arrays (every possible sequence of a given length) can be used for sequencing by hybridization. N-mer arrays can also be used to sort a complex sample. This is particularly advantageous where they are linked to an anchor sequence, for example polyadenylation signal sequence or Poly A tail, or a sequence complementary to a clamp/adaptor sequence that has been ligated to target molecules. Each element of the spatially addressable array will contain a common anchor sequence and a unique member of the N-mer set. These probes can be used in hybridization, primer extension, ligation assays etc. In particular they can be used for priming sequencing by synthesis reactions, where for example the sequence has been fragmented and fragments have been ligated to a clamp. The advantage of the N-mer is that a certain amount of sequence information is already obtained from the target just by hybridization of the N-mer before a sequencing by synthesis reaction has been performed.

Figure 2A:
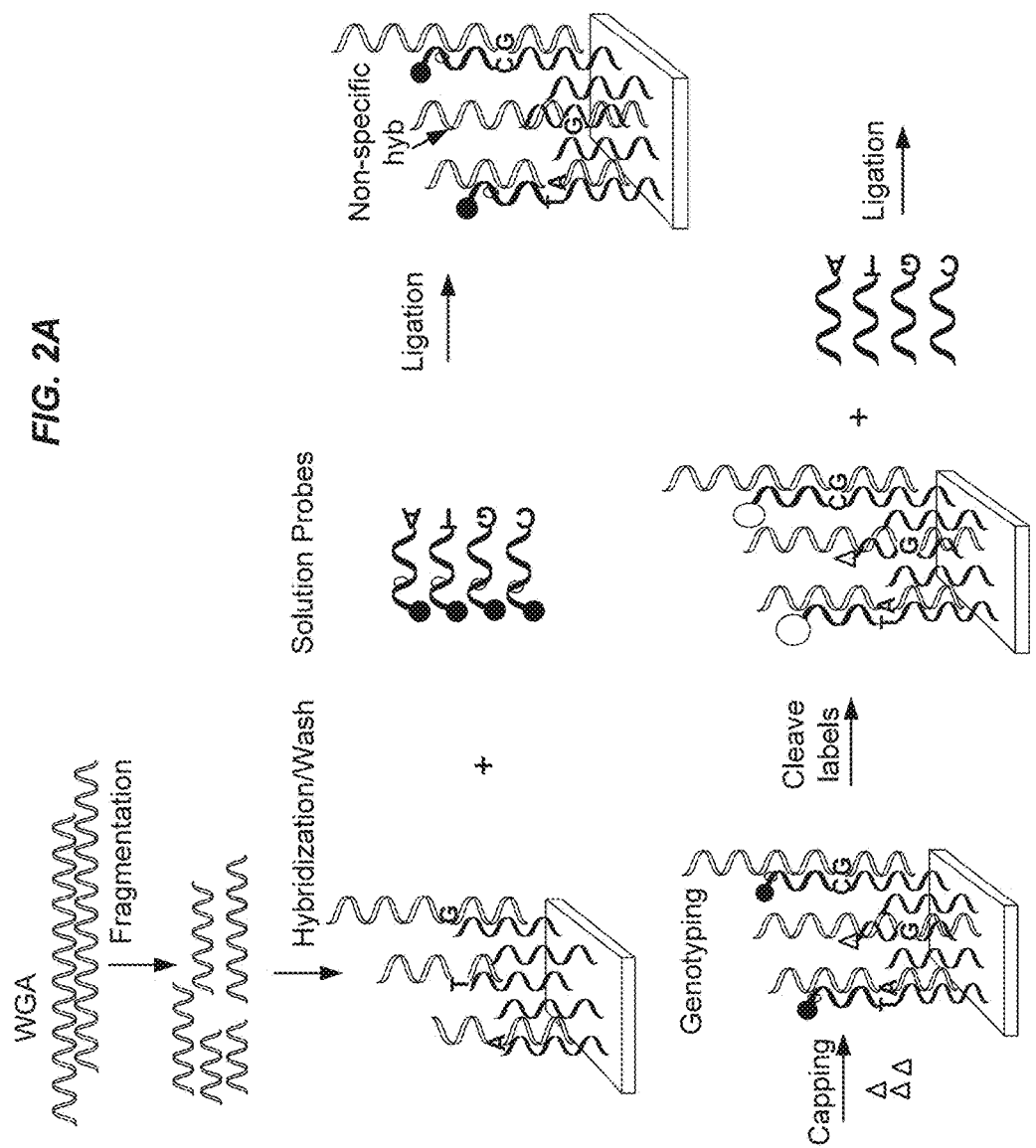
FIG. 2A shows the hybridization, first ligation, capping and cleaving labels steps of the ligation captured sequencing.
Figure 2B:
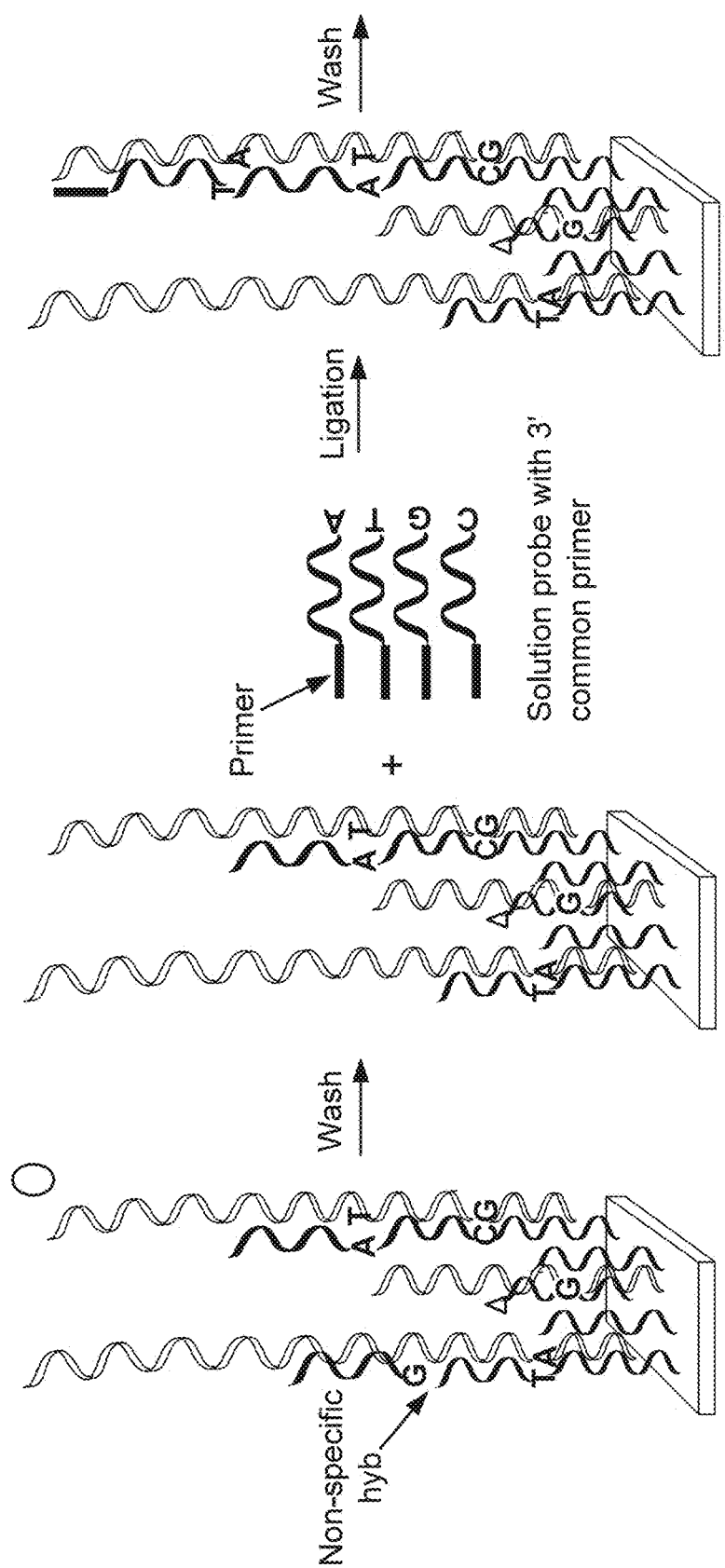
FIG. 2B shows the washing and subsequent ligation steps of the ligation captured sequencing.

The stringency for target-probe hybridization can be adjusted and optimized Hybridization stringency typically refers to the degree to which mismatches are tolerated in a hybridization assay. High stringency is achieved by using a high temperature and low salt concentration. Increasing the concentration of salt and reducing the temperature reduces the hybridization stringency, and enhances the stability of mismatched heteroduplexes. In some embodiments of the present invention, the highest possible stringency in hybridization and washing is used in the subject methods to increase hybridization specificity. In some embodiments of the ligation-captured sequencing, nonspecific hybridization products between a solution probe and the target polynucleotide can be washed off with high-stringency washing. The ionic strength of the buffers used for washing can be adjusted, for example, salt concentration can be lowered for extreme stringency. In some embodiments of the ligation-captured sequencing, the target polynucleotide, for example, genomic DNA can be washed off of the hybridization duplex to allow subsequent primer annealing and base extension (FIG. 2B, C).

Ligation

Figure 2C:
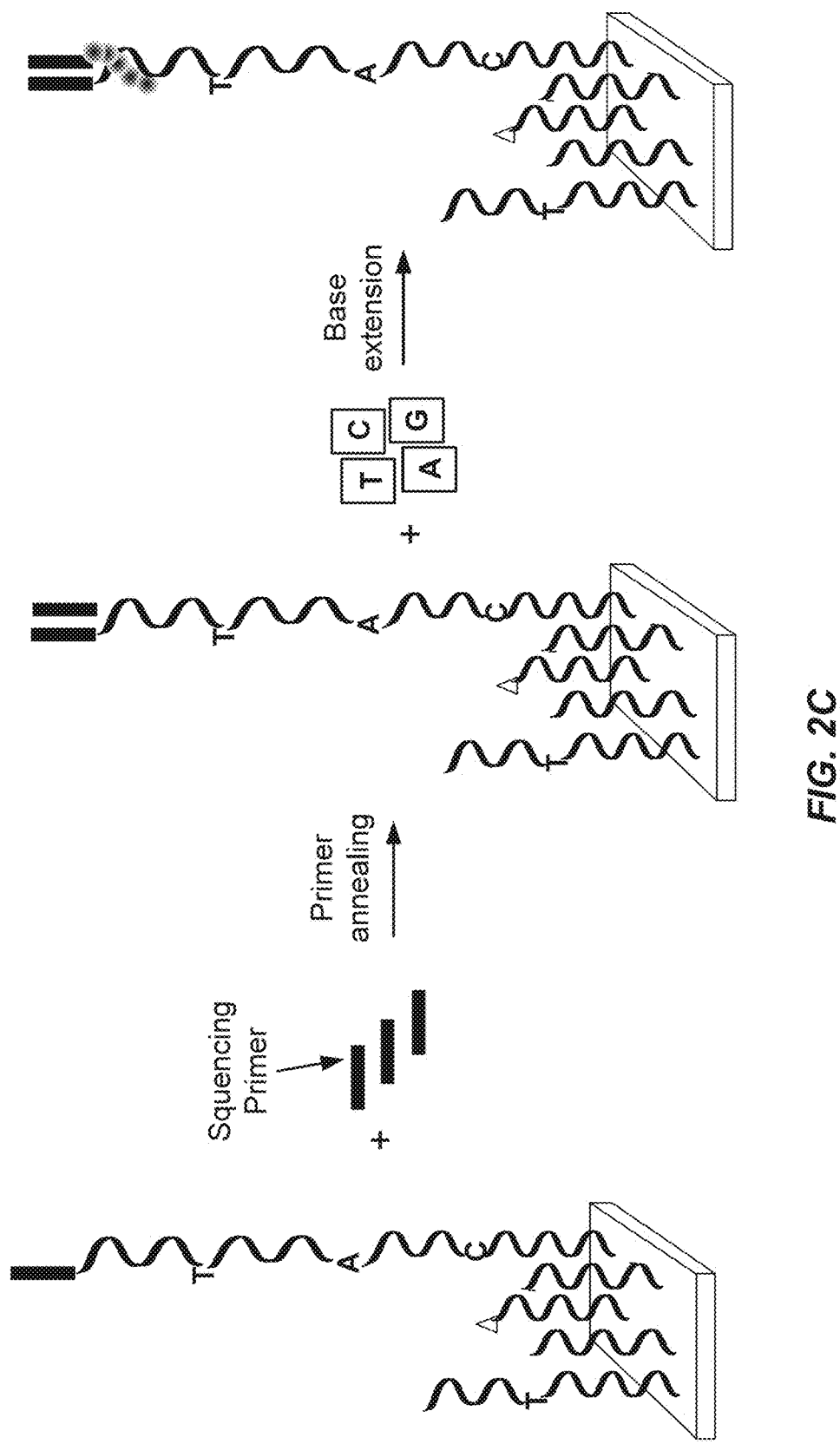
FIG. 2C shows the primer annealing and base extension steps of the ligation captured sequencing.

In one aspect, the present invention provides a ligation-assisted sequencing method in which a first solution is ligated to the capture probe that is attached to the substrate such that the solution probe hybridizes with the target polynucleotide (FIG. 1). In another aspect, the present invention provides a ligation-captured sequencing method comprising the steps depicted in FIG. 2. In some embodiments, a first solution probe hybridizes with the target polynucleotide before capping (FIG. 2A). A subsequent ligation with a second solution probe is performed after cleaving of the cap on the hybridization products, followed by washing of the ligation products to remove nonspecific hybridization products (FIG. 2B). In some embodiments, a third solution probe carrying a common 3' primer is added to allow ligation with the previous solution probe and hybridization between the 3' primer-carrying solution probe and the target polynucleotide. The target polynucleotide can be washed off from the complementary strand which contains the 3' primer. Subsequent primer annealing in the presence of free nucleotides may allow base extension of the complementary strand containing the 3' primer, thereby sequencing the target polynucleotide (FIG. 2C).

Ligation (chemical or enzymatic) provides for improving specificity and for trapping transient interactions. In some embodiments of the subject methods, the target strand is captured by the immobilized oligonucleotide capture probe. An oligonucleotide probe in solution, termed first solution probe, is ligated to the first capture probe, in a target dependent manner. There are several ways that this can be applied. In the first type of assay, the first solution probe is complementary in the region of the known polymorphisms under investigation, the first loci site. One oligo of either the array oligos or the first solution probe overlaps the SNP site and the other ends one base upstream of it. In the second type of assay, the first solution probe comprise the complete set with every sequence of a given length. This allows analysis of every position in the target.

In some embodiments, the first solution probe carries at least one base that is degenerate. Degenerate base typically refers to a position on a DNA sequence that can have multiple possible alternatives. For example, the 5' end of the first solution probe can be either A, T, G, or C. In some embodiments, the first base at 5' end of the first solution probe is degenerate. In some embodiments, the first solution probe is color labeled. The first solution probes carrying A, T, G, or C as the first base at the 5' end can be labeled with different colors such that the first base upon ligation to the probe in hybridization duplex with the target polynucleotide can be known by the color. In some embodiments, the first solution probe carries a cleavage site near its 3' end. Examples of a cleavage site include but are not limited to an amino-2-hydroxypropyl group. The cleavage site on the first solution probe ensures that the cap, i.e. reversible terminator nucleotides on the specific ligation products will be cleaved off while the cap on any non-specific hybridization complexes will remain. In some embodiments, the 3' end of a first solution probe is labeled and the 5' end has a phosphate group. The solution probe may contain 5-50 nucleotides. In some embodiments, the first solution probe contains 5, 6, 7, 8, 9, 10, 11, 12, 13, 14, 15, 16, 17, 18, 19, 20, 21, 22, 23, 24, 25, 30, 35, 40, 45, or 50 nucleotides. In one example, the first solution probe contains 9 nucleotides, i.e. a 9-mer. In another example, the first solution probe is a timer. In another example, the first solution probe is a 15-mer. In some embodiments, degenerate oligos are used as first solution probes. In one example, a degenerate 9-mer is used as the first solution probe. Since each base can be A, T, G, or C, $4^9$ different first solution probes can be generated for specific ligation and hybridization to the target polynucleotide via the methods of the present invention.

One example of a typical ligation reaction is as follows: 5× ligation buffer, 100 mM Tris-HCL pH 8.3, 0.5% Triton X-100, 50 mM MgCl, 250 mM KCl, 5 mM AND+, 50 mM DTT, 5 mM EDTA, solution oligonucleotide 5-10 pmol. *Thermus thermophilus* DNA ligase (Tth DNA ligase) 1 U/ul, target sample, between 37° C. and 65° C. 1 hr. Alternatively, stacking hybridization can be performed first in high salt: 1M NaCl, 3-4.4M TMACl, 5-10 pmol solution oligonucleotide, target sample. After washing of excess reagents from the array under conditions that retain the solution oligonucleotide, the above reaction mix minus solution oligonucleotide and target sample is added to the reaction mix.

The solution probes of the present invention are suitable for ligation when hybridized to the target polynucleotide. During the initial hybridization, the more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Two nucleic acid molecules may be hybridized although the base pairing is not completely complementary. Accordingly, mismatched bases do not prevent hybridization of two nucleic acid molecules provided that appropriate conditions, well known in the art, are used. In the ligation step of the subject method, there is a mismatch which interferes with such ligation when the oligonucleotide probes are hybridized non-specifically to any other nucleotide sequence other than the specific target polynucleotide present in the sample. Thus, the ligation step of the present invention provides higher specificity for the hybridization between the probe and the target polynucleotide. The ligation product of oligonucleotide probes may be distinguished from either individual probes or unspecific hybridization products. In some embodiments, the first solution probe, the probe-target polynucleotide complexes, the unspecific hybridization products, and a ligase are mixed to form a ligase detection reaction mixture to carry out the ligation reaction.

In some embodiments, the ligase detection reaction mixture is subjected to one or more ligase detection reaction cycles having a denaturation treatment and hybridization treatment substantially as described above. In the hybridization treatment, the probe hybridizes at adjacent positions in a base-specific manner to the respective target polynucleotide if present. As a result, adjacent probes ligate to the target polynucleotide to form a ligation product sequence. The ligation product may contain a detectable reporter label. The solid-phase bound oligonucleotide probe (capture probe) may have hybridized to nucleotide sequences other than the respective complementary target polynucleotides but do not ligate together with the solution probe due to the presence of one or more mismatches and individually separate during the denaturation treatment. In some embodiments, following the ligation detection reaction cycles, the reporter labels of the ligation product can be detected which indicates the presence of one or more target nucleotide sequences in the sample. Desirably, the first solution probe and capture probe, or adjacent additional solution probes (such as the first and second or second and third solution probes) are suitable for ligation together at a ligation junction when hybridized to a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. In some embodiments, the mismatch is at the base adjacent to the 3' base at the ligation junction. Alternatively, the mismatch can be at the bases adjacent to bases at the ligation junction.

One example of a ligation reaction of the subject method is illustrated as follows. After denaturation of the target nucleic acid, if present as a double stranded DNA molecule, at a temperature of 80-105° C., preferably 94° C., ligation detection reaction oligonucleotide probes for one strand of the target nucleotide sequence are added along with a ligase, for example, a thermostable ligase such as *Thermus aquaticus ligase*. The oligonucleotide probes are then allowed to hybridize to the target nucleic acid molecule and ligate together, typically, at a temperature of 45-85° C., preferably, 65° C. When there is perfect complementarity at the ligation junction, the oligonucleotides can be ligated together. Where the variable nucleotide is T or A, the presence of T in the target nucleotide sequence will cause the oligonucleotide probe with the F1 reporter label to ligate to the common oligonucleotide probe with the 5' poly A tail $A_n$, and the presence of A in the target nucleotide sequence will cause the oligonucleotide probe with the F2 reporter label to ligate to the common oligonucleotide probe with $A_n$. Similarly, where the variable nucleotide is A or G, the presence of T in the target nucleotide sequence will cause the oligonucleotide probe with F3AA reporter label (i.e. the F3 reporter label coupled to 2 additional bases forming a 5' poly A spacer) to ligate to the common oligonucleotide probe with the 5' poly A tail $A_{n+4}$, and the presence of C in the target nucleotide sequence will cause the oligonucleotide probe with the F3 reporter label to ligate to the common oligonucleotide probe with the 5' poly A tail $A_{n+4}$. Following ligation, the material is again subjected to denaturation to separate the hybridized strands. The hybridization/ligation and denaturation steps can be carried out through one or more cycles (e.g., 1 to 50 cycles) to amplify target signals. Equimolar ligation of both F3-labeled oligonucleotides indicates the individual is heterozygous for that locus, whereas ligation of only the F2 labeled oligonucleotides indicates the individual is homozygous for the other locus.

The ligase detection reaction is described generally in WO 90/17239 to Barany et al., F. Barany et al., "Cloning, Overexpression and Nucleotide Sequence of a Thermostable DNA Ligase-encoding Gene," Gene, 109:1-11 (1991), and F. Barany, "Genetic Disease Detection and DNA Amplification Using Cloned Thermostable Ligase," Proc. Natl. Acad. Sci. USA, 88:189-193 (1991), the disclosures of which are hereby incorporated by reference. In accordance with the present invention, the ligase detection reaction can use 2 sets of complementary oligonucleotides. This is known as the ligase chain reaction which is described in the 3 immediately preceding references, which are hereby incorporated by reference. Alternatively, the ligase detection reaction can involve a single cycle which is known as the oligonucleotide ligation assay. See Landegren, et al., "A Ligase-Mediated Gene Detection Technique," Science 241:1077-80 (1988); Landegren, et al., "DNA Diagnostics-Molecular Techniques and Automation," Science 242:229-37 (1988); and U.S. Pat. No. 4,988,617 to Landegren, et al., which are hereby incorporated by reference. During ligase detection reaction phases, the denaturation treatment can be carried out at a temperature of 80-105° C., while hybridization can take place at 50-85° C. Each cycle may comprise a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase is 1 to 250 minutes. The oligonucleotide probe sets or primers can be in the form of ribonucleotides, deoxynucleotides, modified ribonucleotides, modified deoxyribonucleotides, modified phosphate-sugar-backbone oligonucleotides, nucleotide analogs, and mixtures thereof. The oligonucleotide probe sets or primers may have a reporter label suitable for detection. Useful labels include but are not limited to chromophores, fluorescent moieties, enzymes, antigens, heavy metals, magnetic probes, dyes, phosphorescent groups, radioactive materials, chemiluminescent moieties, and electrochemical detecting moieties.

One example of a ligase that can be used in the present invention is thermostable ligase derived from *Thermus aquaticus* (M. Takahashi, et al., "Thermophillic DNA Ligase," J. Biol. Chem. 259:10041-47 (1984)), which is hereby incorporated by reference. Alternatively, it can be prepared recombinantly. Procedures for such isolation as well as the recombinant production of *Thermus aquaticus* ligase (as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," Gene 109:1-11 (1991), which are hereby incorporated by reference. These references contain complete sequence information for this ligase as well as the encoding DNA. Other suitable ligases include but are not limited to *E. coli* ligase, T4 ligase, and *Pyococcus ligase*.

The ligation detection reaction mixture may include a carrier DNA, such as salmon sperm DNA. The hybridization step in the ligase detection reaction, which is preferably a thermal hybridization treatment discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

Capping and Sequencing by Synthesis

In general, after the ligation step the non-specific hybridization is eliminated by a washing step. Thus, the only target polynucleotide captured are the allele and/or locus specific and are subject to sequencing using methods known in the art, preferably by sequencing-by-synthesis.

In some embodiments, the subject methods of the present invention comprise a capping step after the first ligation of the first solution probe to the target polynucleotide prevent base extension occurring in complexes formed by non-specific hybridization. For example, nonspecific hybridization may occur between an allele-specific oligo probe and the target polynucleotide. In some embodiments, the capping of the hybridization products uses nucleotide reversible terminators. Nucleotide reversible terminators prevent sequencing by synthesis. The array can be designed in such a way that each spot captures a consecutive fragment of DNA from the genome. For example probes can be 10-100 bases apart in the genome (or the part of the genome of interest). The intervening sequence can then be determined by sequencing by synthesis methods known in the art (for example, see WO9844152). The probes can also be part of an N-mer as disclosed herein. The underlying theory of procedures according to the invention is that, contrary to natural primer mediated template directed complementary DNA synthesis, only one base can be added at one time. Further additions are prevented by, for example, a blocking group such as a nucleotide reversible terminator, similar to having protecting groups in automated chemical DNA synthesis. The base added to each single molecule is detected and recorded after base addition. The blocking group such as a nucleotide reversible terminator is then removed allowing the next base to be added. As well as base by base, the procedure can also be performed dinucleotide by dinucleotide or oligomer by oligomer of any convenient length.

Nucleotide reversible terminators are nucleotide analogues, which are modified with a reversible chemical moiety capping the 3'-OH group to temporarily terminate the polymerase reaction. In this way, only one nucleotide is incorporated into the growing DNA strand even in homopolymeric regions. For example, the 3' end can be capped with an amino-2-hydroxypropyl group. An allyl or a 2-nitrobenzyl group can also be used as the reversible moiety to cap the 3'-OH of the four nucleotides. Examples of reversible terminators include but are not limited to 3'-O-modified nucleotides such as 3'-O-allyl-dNTPs and 3'-O-(2-nitrobenzyl)-dNTPs. After detection of the cleavage site present on the solution probe, the 3'-OH of the primer extension products is regenerated through different deprotection methods. The capping moiety on the 3'-OH of the DNA extension product can be efficiently removed after detection of a cleavage site by a chemical method, enzymatic reaction or photolysis, i.e. the cap will be cleaved from the cleavage site. To sequence DNA, in some embodiments, templates containing homopolymeric regions are immobilized on Sepharose beads, and then extension—signal detection—deprotection cycles are conducted by using the nucleotide reversible terminators on the DNA beads to unambiguously decipher the sequence of DNA templates. In some embodiments, this reversible-terminator-sequencing approach is used in the subject methods to accurately determine DNA sequences. (The cap may be referred to herein as a "protective group").

In some embodiments, the nucleotide reversible terminators are labeled with colors, for example, flurophores in four colors. In some embodiments, the nucleotide reversible terminator read length is at least 15 bases.

Base Extension

After the cap has been cleaved, base extension of the probe can be performed to continue the sequencing of the target polynucleotide. The base extension begins at the 3' end of the most distal solution probe from the capture probe (FIG. 1).

Primer extension is another means for improving specificity of hybridization and genotyping at the free end of the immobilized probe and for trapping transient interactions. In general, the primers used according to the methods of the invention embrace oligonucleotides of sufficient length and appropriate sequence which provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15-22 or more nucleotides, although it may contain fewer nucleotides as long as the primer is of sufficient specificity to allow essentially only the amplification of the specifically desired target nucleotide sequence (i.e., the primer is substantially complementary). The exact length of primer will depend on many factors, including temperature, buffer, and nucleotide composition. "Substantially complementary" refers to that the primers are sufficiently complementary to hybridize with their respective strands under conditions which allow the agent for polymerization to function. In other words, the primers should have sufficient complementarily with the flanking sequences to hybridize with and permit amplification of the nucleotide sequence. Preferably, the 3' terminus of the primer that is extended has perfectly base paired complementarity with the complementary flanking strand. The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

More than one way of primer extension can be applied. The first is the multi-primer approach, where there are separate array elements containing single molecules for each allele. The second is the multi-base approach in which a single array contains a single species of primer whose last base is upstream of the polymorphic site. The different alleles are distinguished by incorporation of different bases each of which is differentially labeled. This approach is also known as mini-sequencing. For example, the following reaction mix and conditions can be used: 5×polymerase buffer, 200 mM Tris-HCl pH 7.5, 100 mM $MgCl_2$, 250 mM NaCl, 2.5 mM DTT; ddNTPs or dNTPs (multibase); dNTPs (multiprimer), Sequenase V.2 (0.5 μ/μl) in polymerase dilution buffer, target sample, 37° C. 1 hr. It can be advantageous to label the primer/capture probe to lend more confidence to an extension signal, if it co-localizes with labeled capture probe. Preferably no cold dNTP corresponding to the labeled dNTP is added. An exo-polymerase, for example, thermosequenase (Amersham) or Taquenase (Promega), can be used. The target can be capture immobilized and synthesis primed using an upstream primer. Multiple primers can prime synthesis at several points along the captured target. The target may or may not be horizontalized.

In some embodiments, in the polymerase chain reaction, one or a plurality of oligonucleotide primer sets can be provided. Each set can have an upstream primer containing the same sequence as the 5' upstream primer-specific portion of the ligation product sequence and a downstream primer complementary to the 3' downstream primer-specific portion of the ligation product sequence, where one primer has a detectable reporter label. In some embodiments, the ligase detection reaction mixture is blended with the one or a plurality of oligonucleotide primer sets and the polymerase to form a polymerase chain reaction mixture.

In some embodiments, the polymerase chain reaction mixture is subjected to one or more polymerase chain reaction cycles which include a denaturation treatment, a hybridization treatment, and an extension treatment. During the denaturation treatment, hybridized nucleic acid sequences are separated. The hybridization treatment causes primers to hybridize to their complementary primer-specific portions of the ligation product sequence. During the extension treatment, hybridized primers are extended to form extension products complementary to the sequences to which the primers are hybridized. In a first cycle of the polymerase chain reaction phase, the downstream primer hybridizes to the 3' downstream primer-specific portion of the ligation product sequence and is extended to form an extension product complementary to the ligation product sequence. In subsequent cycles, the upstream primer hybridizes to the 5' upstream primer-specific portion of the extension product complementary to the ligation product sequence and the 3' downstream primer hybridizes to the 3' downstream portion of the ligation product sequence. Following the polymerase chain reaction phase of this process, the reporter labels are detected and the extension products are distinguished to indicate the presence of one or more target nucleotide sequences in the sample.

The polymerase chain reaction process is fully described in H. Erlich, et. al., "Recent Advances in the Polymerase Chain Reaction," Science 252: 1643-50 (1991); M. Innis, et. al., PCR Protocols: A Guide to Methods and Applications, Academic Press: New York (1990); and R. Saiki, et. al., "Primer-directed Enzymatic Amplification of DNA with a Thermostable DNA Polymerase," Science 239: 487-91 (1988), which are hereby incorporated by reference.

Signal Detection and Imaging

In some embodiments, the subject methods provide sensitive signal detection that can detect at least hundreds of molecules with high resolution. In one embodiment, the subject methods can detect one molecule. In another embodiment, the subject methods can detect approximately 10 molecules. For example, the subject methods can detect 10, 11, 12, 13, 14, 15, 16, 17, 18, 19, 20 or more molecules. The ability of the subject methods to detect about 10-20 molecules can be critical to enable highly stringent washing as described herein. Without being bound by any theory, it is believed that highly stringent washing can wash off all or substantially all of the non-specific binding while leaving a few number of specific target molecules hybridized within the array feature of the present invention. In some embodiments, a highly sensitive detector, e.g. the Helicos system, can be used to detect the few molecules, e.g. 10-20 molecules that are specifically bound to the target polynucleotide.

Polynucleotide of the invention may be labeled. In some embodiments, a molecule or compound has at least one element, isotope or chemical compound attached to enable the detection of the compound. In general, labels of use in the invention include without limitation isotopic labels, which may be radioactive or heavy isotopes, magnetic labels, electrical labels, thermal labels, colored and luminescent dyes, enzymes and magnetic particles as well. Dyes of use in the invention may be chromophores, phosphors or fluorescent dyes, which due to their strong signals provide a good signal-to-noise ratio for decoding.

Many embodiments of the invention include the use of fluorescent labels. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 6th Edition of the Molecular Probes Handbook by Richard P. Haugland, hereby expressly incorporated by reference in its entirety for all purposes and in particular for its teachings regarding labels of use in accordance with the present invention. Commercially available fluorescent nucleotide analogues readily incorporated into the labeling oligonucleotides include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14- dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others).

A number of multiplex detection formats can be used, including either labeled/tagged bead sets (e.g., those produced by Luminex), in which each label is assigned to the individual probe-specific primer, or oligonucleotide arrays on slides, in which in which specific oligonucleotide spot/position is assigned to the individual probe-specific primer. The limited sequence complexity of the recovered target-specific probes provides conditions for easier and higher level multiplexing, especially using with universal and Zipcode/ID sequence tags. After the hybridization of the primers to the target-probe complex, the primers are extended by a nucleotide polymerase. Polymerase chain reaction is a technique well known in the relevant art. In certain embodiments, the polymerase is selected from an RNA polymerase and a reverse transcriptase.

Where an array is utilized, the detection phase of the process may involve scanning and identifying target polynucleotide sequences in the test sample. Scanning can be carried out by scanning probe microscopy (SPM) including scanning tunneling microscopy (STM) and atomic force microscopy (AFM), scanning electron microscopy, confocal microscopy, charge-coupled device, infrared microscopy, electrical conductance, and fluorescent or phosphor imaging, for example fluorescence resonance energy transfer (FRET). Optical interrogation/detection techniques include but are not limited to near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques can also be used in a spectroscopic mode. The actual detection means include charge coupled device (CCD) cameras and intensified CCDs, photodiodes and photomultiplier tubes. These means and techniques are well-known in the art. Various detection methods are disclosed in U.S. Patent Application Publication No. US 2004/0248144, which is herein incorporated by reference.

For multicolor imaging, signals of different wavelength can be obtained by multiple acquisitions or by simultaneous acquisition by splitting the signal, using RGB detectors or analyzing the whole spectrum (Richard Levenson, Cambridge Healthtech Institutes, Fifth Annual meeting on Advances in Assays, Molecular Labels, Signaling and Detection, May 17-18$^{th}$ Washington D.C.). Several spectral lines can acquired by the use of a filter wheel or a monochromater. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

Figure 7:
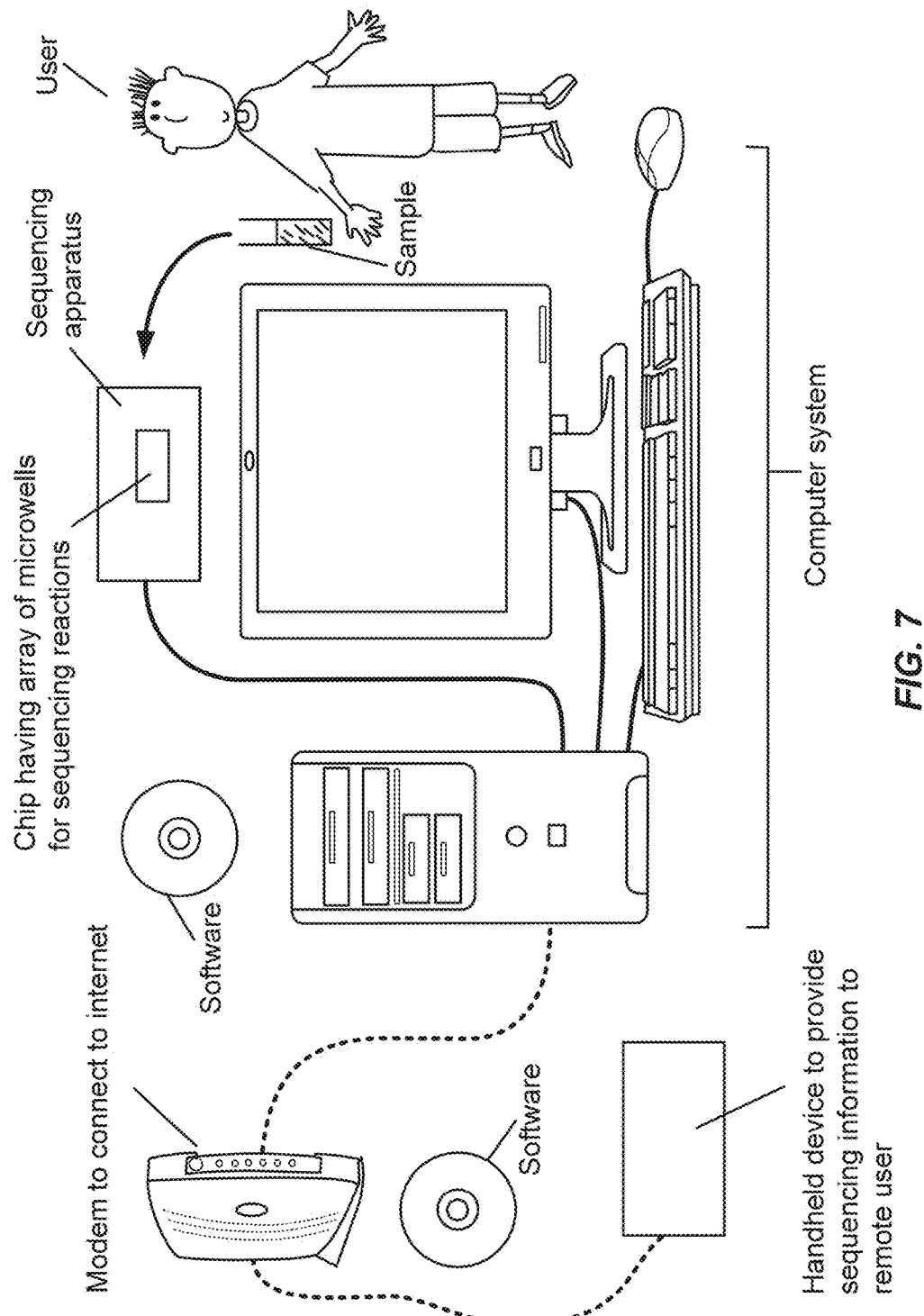
FIG. 7 shows that nucleic acid sequence information can be obtained, processed, analyzed and/or assembled via a computer system.
Figure 9:
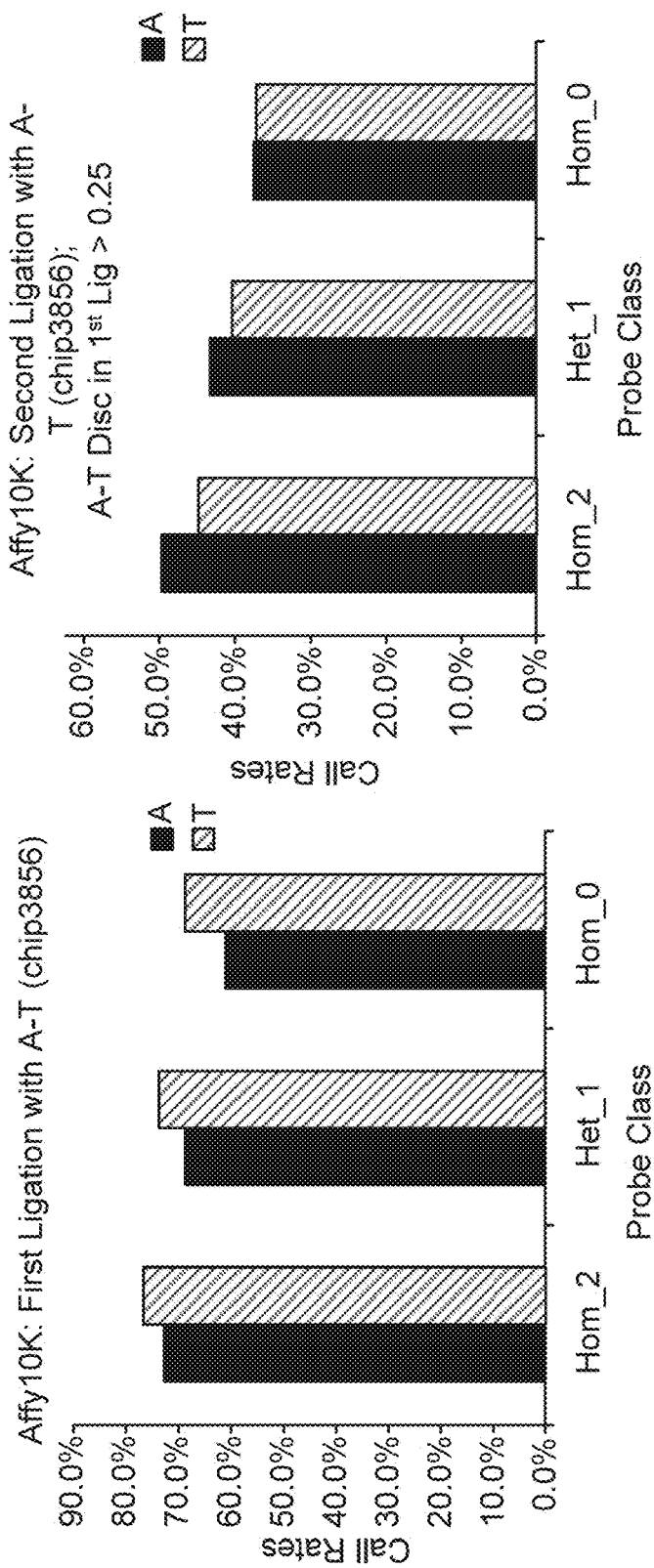
FIG. 9 shows results from sequencing reactions on a human SNP chip.

Processing of Raw Data and Analysis of Genetic Information with Computer Algorithm Typically, identifying target polynucleotide sequence and integrating sequences to assemble genomic information is carried out with a computer (FIG. 7). In some embodiments, the present invention also encompasses computer software or algorithm designed to analyze and assemble sequence information obtained via the methods of the present invention.

In terms of sequence read interpretation for the "in situ" arrays, reads at array features correspond to X-Y coordinates that map to the loci of interest. A "read" typically refers to an observed sequence derived from raw data, such as the order of detected signals corresponding to the cyclical addition of individual nucleotides. In some embodiments, the reads are checked against the expected reference genome sequence at the 10-bp loci for quality control. A reference sequence enables the use of short read length. Reads that have passed the quality control check are then combined to generate a consensus sequence at each locus. In one example, there are 10 unique probes per locus of interest minus any reads that have failed the quality control checks.

In terms of sequence read interpretation for the "lawn" approach, the reads are at random locations on a surface, e.g. a flow cell. In some embodiments, the reads are checked against the expected subset of reference genome sequence at the loci of interest for quality control. Reads that have passed the quality control check are mapped to the individual locus of interest. Reads corresponding to each locus are then combined to generate a consensus sequence. In one embodiment, there are more than 3,000 reads per 10-bp locus.

In some embodiments, the present invention provides a method for sequencing a genome by generating reads that are greater than 5, 10, 15, 20, 30, 40, 50, 60, 74, 100, 150 bases. In some embodiments, the subject methods encompass sequencing a genome by sequencing a lawn of randomly placed probes, wherein each probe generates a read that is greater than 5 bases. The length of the reads is generally longer than the reads generated via other nucleotide sequencing techniques currently available. In other embodiments, the reads generated via the methods of the present invention can be 10, 11, 12, 13, 14, 15, 16, 17, 18, 19, 20, 21, 22, 23, 24, 25, 30, or more bases long.

In some embodiments, heterozygous insertions/deletions (indels) can be read and analyzed via the methods of the present invention (FIG. 6). Indels (insertions/deletions) are important DNA sequence variations because of the high frequency in the human genome, the deleterious effects on the reading frame and protein expression, and the association with disease and disease susceptibility of common diseases. In a recent study with a human individual with the whole genome sequenced, 292,102 heterozygous indels and 559,473 homozygous indels were identified. Decrypting such a large number of heterozygous indels is computationally intensive and requires efficient algorithms. In some embodiments of the "in situ" array of the present invention, probes have both maternal and paternal chromosome hybridized. The forward probe reads and the reverse probe reads of a paternal 3-base insertion are shown in FIG. 6. In some embodiments of a "lawn" flow cell, each probe has either maternal or paternal chromosome hybridized.

In some embodiments, copy number polymorphisms can be read and analyzed using the methods of the present invention. Copy number polymorphisms are present at CNVs of genomic DNA, for example, a 10-bp region within a larger common CNV. Count of reads at CNV can be proportional to an integer copy number. Copy number call can be based on comparison to estimated diploid read counts from all loci. The methods of the present invention do not generally map breakpoints.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. No. 60/364,731 and in PCT Application PCT/US99/06097 (published as WO99/47964), each of which also is hereby incorporated by reference in its entirety for all purposes. Fluorescence imaging and software programs or algorithms for DNA sequence analysis and read interpretation are known to one of ordinary skill in the art and are disclosed in Harris T D, et al. "Single-Molecule DNA Sequencing of a Viral Genome" *Science* 4 Apr. 2008: Vol. 320. no. 5872, pp. 106-109, which is herein incorporated by reference in its entirety. In some embodiments, Phred software is used for DNA sequence analysis. Phred reads DNA sequencer trace data, calls bases, assigns quality values to the bases, and writes the base calls and quality values to output files. Phred is a widely-used program for base calling DNA sequencing trace files. Phred can read trace data from SCF files and ABI model 373 and 377 DNA sequencer chromat files, automatically detecting the file format. After calling bases, phred writes the sequences to files in either FASTA format, the format suitable for XBAP, PHD format, or the SCF format. Quality values for the bases are written to FASTA format files or PHD files, which can be used by the phrap sequence assembly program in order to increase the accuracy of the assembled sequence. The quality value is a log-transformed error probability, specifically $Q=-10 \log_{10}(P_e)$ where Q and $P_e$ are respectively the quality value and error probability of a particular base call. The phred quality values have been thoroughly tested for both accuracy and power to discriminate between correct and incorrect base-calls. Phred can use the quality values to perform sequence trimming.

Discrete groups of assay classification (e.g. nucleotide base calling) can be defined by various measures. A set of unique parameters are chosen to define each of several discrete groups. The result of interrogation of each individual molecule can be assigned to one of the discrete groups. One group can be assigned to represent signals that do not fall within known patterns. For example there may be groups for real base additions, a, c, g, and t in extension assays.

The single molecule approach enables direct counting and classification of individual events. A general algorithm for single molecule counting, once the single molecules have been labeled by, for example, thresholding, is:
Loop through all pixels, p(x,y) left to right, top to bottom
If p(xy)=0, do nothing
If p(xy)=1, add to counter In some embodiments, the methods of this invention require basic image processing operations and counting, measuring and assignment operations to be performed on the raw images that are obtained. The invention includes the adaptation and application of general methods including software and algorithms, known in the art for digital signal processing, counting, measuring and making assignments from the raw data. This includes Bayesian, heuristic, machine learning and knowledge based methods. Moreover, digital data processing facilitates error correction and temporal resolution of reactions at the array surface. Thus, time-resolved microscopy techniques can be used to differentiate between bona-fide reactions between probe and sample and "noise" due to aberrant interactions which take place over extended incubation times. The use of time-gated detection or time-correlated single-photon counting is particularly preferred in such an embodiment.

In some embodiments, the present invention also provides a method for sorting signals obtained from single molecule analysis according to the confidence with which the signal may be treated. A high confidence in the signal leads to the signal being added to a PASS group and counted; signals in which confidence is low are added to a FAIL group and discarded, or used in error assessment and as a resource for assay design (for example the propensity of a particular primer sequence to give rise to errors in primer extension, can be used to inform primer design in future experiments.

The reaction is controlled by adjusting reaction components, for example salt concentration, ddNTP concentration, temperature or pH such that the incorporations occur within the time window analyzed. A subroutine can be included to check that the fluorescence shows single-step photobleaching characteristic, but ignoring short-scale fluctuations which are likely to be due to blinking. If a single dye molecule, which photobleaches after a time, is associated with each ddNTP, then an additional sub-process/routine can be added which eliminates signals that after an initial burst re-occur in the same pixel after such a number of time points that the absence cannot be attributed to blinking. This is likely to be non-specific absorption at the same foci as a legitimate extension. A sub-routine can be included to eliminate any fluorescence that occurs in multiple filters, above the level expected for the dye being analyzed. Fluorescence due to a single dye molecule can be distinguished from particulate contamination by analyzing the concentration dependence of the signal. This can be done if each sequence is arrayed at two or more concentrations. Signals that remain at equal concentration across the array dilution are artifacts, and real signals are those whose frequency changes in line with changes in array probe concentration. If the array is composed of elements an additional process can be used to organize the data into groupings representing the array elements. In some embodiments, detection events are generated by labeling the sample nucleic acids and/or the probe molecules, and imaging the labels on the array using a suitable detector. Preferred labeling and detection techniques are described herein.

In some embodiments, the present invention also encompasses computer algorithm or software designed to analyze and assemble genomic information obtained via the methods of the present invention. In some embodiments, information on SNPs, CNVs, or DMET markers of a sample is obtained via the methods of the present invention.

During the initial hybridization, non-specific strand can be captured by the array probes. Using the ligation assisted or ligation captured methods of the present invention, the non-specific hybridization complexes can be easily eliminated from further sequencing. Regions of the genome that are known to be duplicated or repetitive may be avoided. In some embodiments, the use of markers other than the labels may aid in the integration of genomic information from pieces of target polynucleotide strands, for example, marking the ends of the molecule or other sites, including SNP sites with markers that can be distinguishable from the SNP color tags.

In some embodiments, specificity of read mapping can be increased by ranking probes based on number of hits to a reference genome. For example, in silico, tally hit counts of 15 to 20 base reads at X % identity, where X can vary from 95 to 99%. Empirically, defined subsets of probes can be run in experiments to determine the number of read hits to regions other than the locus of interest. Based on the results from a number of subsets, the problematic probes or loci can be assessed. In other embodiments, high hit count probes or loci can be mitigated. For example, these high hit count probes can be replaced with nearby probe sequences. It may require longer read lengths if new probes are further away from the locus of interest. In another embodiment, problematic probes or loci can be grouped and run in separate flow cell to maintain high read mapping accuracy for non-problematic probes. This may increase costs due to the need to run more than one flow cell per sample and the need to manufacture flow cells with different sets of probes. In another embodiment, the problematic loci may be omitted from the panel.

II. Ligation Captured Sequencing

Another aspect of the present invention relates to a method for determining or identifying nucleotide sequence via ligation captured sequencing. This method generally comprises the steps of a) immobilizing a set of loci-specific probes (also referred to as "capture probes") on a substrate, wherein the probes have defined sequences; b) hybridizing a sample containing a target polynucleotide to the set of allele-specific probes; c) ligating a first solution probe to the loci-specific probe, wherein the solution probe carries a cleavage site and hybridizes to the target polynucleotide; d) providing a nucleotide reversible terminator to the hybridization duplexes resulted from steps b) and c), wherein the nucleotide reversible terminator prevents base extension of nonspecific hybridization complexes; e) cleaving the nucleotide reversible terminator at the cleavage site present on the solution probe to allow further hybridization; f) ligating a second solution probe to the first solution probe such that the second solution probe hybridizes to the target polynucleotide; g) washing the hybridization duplexes from step f) to remove nonspecific hybridization between the second solution probe and the target polynucleotide; h) ligating a set of solution probes carrying a common primer at 3' end to the previously ligated solution probe such that the solution probe carrying the primer hybridizes to the target polynucleotide; i) washing the hybridization duplexes from step h) to remove the target polynucleotide from the hybridization duplexes; j) adding primers that are complementary to the common primer sequence at 3' end of the solution probes to allow primer annealing; and k) placing the single strand probe polynucleotide under nucleic acid synthesis conditions in the presence of free nucleotides to allow base extension from the annealed primer at the 3' end based on nucleic acid sequence of the probe strand that is complementary to the target polynucleotide. In some embodiments, the method further comprises obtaining sequence information of the target polynucleotide via a computer system. In some embodiments, the target polynucleotide is genomic DNA. In some embodiments, the solution probes are labeled and have at least one base that is degenerate. For example, the first base at 5' end of the solution probes is degenerate, i.e. it can be A, T, G, or C. In one embodiment, the solution probe is a 9-mer, i.e. contains 9 nucleotides. In some embodiments, the washing condition is sufficiently stringent such that the solution probes that have nonspecifically hybridized to the target polynucleotide can be washed off. In other embodiments, the washing condition is sufficiently stringent such that the target polynucleotide can be washed off from the hybridization duplex. The cycle of ligation between the solution probes and the hybridization between solution probes and the target polynucleotide followed by stringent washing to remove nonspecific ligation can be repeated more than one time. The subject ligation-captured sequencing method provides higher hybridization specificity. The specificity can be at least 95%, 96%, 97%, 98%, 99%, 99.5% or more.

In some embodiments, ligation-captured sequencing comprises ligating a second set of solution probes to the probe-target duplexes after cleaving of the 3' end reversible terminator to form double ligated probe-target duplexes, as depicted in FIG. 2B. Nonspecific hybridization between the second solution probe and the target polynucleotide may form. In some embodiments, the double ligation step is followed by washing. The hybridization products resulted from the second ligation reaction can be washed by non-stringent wash and stringent wash. For example, non-stringent wash is normally 2×SSC, 65° C., Eff $T_m$=81.5+16.6 [log(0.33)]+0.41(45%)=92.0° C., % Homology=100−[(92−65)/1.4]=80.7%. An example of stringent wash can be 0.1×SSC, 65° C., Eff $T_m$=81.5+16.6[log(0.0165)]+0.41 (45%)=70.4° C., % Homology=100−[(70.4−65)/1.4]= 96.1%. Changes in temperature and salt concentrations affect the stringency of washes and therefore the hybridization specificity. Determining the stringency of washes after polynucleotide hybridization is well within the knowledge of one skilled in the art. In some embodiments, the washing condition is sufficiently stringent such that the second solution probes that have nonspecifically hybridized to the target polynucleotide can be washed off.

In some embodiments, the ligation step f) and the subsequent washing step g) can be repeated more than one time. For example, the ligation reaction with a solution probe followed by stringent washing to remove nonspecific hybridization can be performed 2, 3, 4, 5 times or more. The hybridization specificity can be enhanced via multiple rounds of ligation as disclosed herein.

In some embodiments, the ligation duplexes resulted from step g) are then provided with another set of solution probes which carry a common primer at 3' end. These primer-carrying solution probes can be labeled with different colors and have at least one degenerate base. In some embodiments, the first base at 5' end of the primer-carrying solution probes is degenerate, i.e. it can be A, T, G, or C. In some embodiments, the primer-carrying solution probes ligate to the previously ligated solution probe and hybridize to the target polynucleotide as depicted in FIG. 2B. This ligation between the primer-carrying solution probe and the target polynucleotide can be followed by stringent washing. In some embodiments, the washing condition is sufficiently stringent such that all the target polynucleotides can be washed off from the hybridization duplexes, leaving only the probe strands attached to the substrate, as shown in FIG. 2C. The probe strand is complementary to the target polynucleotide.

In some embodiments, in the subsequent step (i.e. step j), primers that are complementary to the common 3' end primer present on the solution probes are added to the single-stranded probe strand, which is complementary to the target polynucleotide, to allow primer annealing. After the primers have annealed, free labeled nucleotides can be added under nucleic acid synthesis conditions to allow base extension from the annealed primer at the 3' end based on the sequence of the probe strand that is complementary to the target polynucleotide. In this way, the nucleic acid sequence of the target polynucleotide can be accurately determined.

In some embodiments, the sequence of the target polynucleotide is determined from 5' end. In other embodiments, the sequence of the target polynucleotide is determined from 3' end.

III. Utility

The methods of the present invention provide several advantages. First, the loci- and allele-specific, sequence-known probes provide a superior combination of efficiency, sensitivity and specificity of hybridization: they provide for hybridization that exceeds the sequence-specificity of ordinary short oligonucleotide probes, that exceed the kinetics of ordinary long oligonucleotide probes, that exceeds the affinity to polynucleotide and oligonucleotide target, and that exceeds the sensitivity (signal-to-noise ratio) of ordinary short and long oligonucleotide probes. Furthermore, they are SNP capable, and can carry multiple signal-reporting labels or ligands, provide for a higher level of multiplexing of diverse target sequences.

In addition, the ligation-assisted sequencing or ligation-captured sequencing comprising ligation of target polynucleotide with solution probes, capping of the 3' end of hybridization duplexes, specific cleaving of the 3' cap on nonspecific hybridization products, and/or subsequent ligation with the solution probes, stringent washing and primer extension of the complementary strand provide higher hybridization specificity and ensure more accurate sequencing of the target polynucleotide. The hybridization specificity achieved via the methods of the present invention is at least 95%, 96%, 97%, 98%, 98.5%, 99%, 99.5% or more. The present invention provides low-cost, high-throughput and accurate methods for sequencing target polynucleotide.

Moreover, the methods of the invention can be multiplexed to a very high degree. Samples can comprise pooled genomes of target and control subject populations respectively, since accurate analysis of allele frequencies can be accurately determined by single molecule counting. Since more than a single site on each molecule can be probed, haplotype information is easily determined. There is also the possibility of obtaining haplotype frequencies. Such methods are particularly applicable in association studies, where SNP frequencies are correlated with diseases in a population. The expense of single SNP typing reactions can be prohibitive when each study requires the performance of millions of individual reactions; the present invention permits millions of individual reactions to be performed and analyzed on a single array surface.

The methods of the present invention are useful in identifying high value polymorphisms located in regulatory elements and coding regions for a number of drug metabolizing enzyme and transporter (DMET) genes. Expression of these DMET genes will give information on the absorption, distribution, metabolism, and excretion profiles of a drug. Interpretation of complex transcriptional responses to various drugs and subsequent prediction of physiological effects is important for the development of effective therapeutics. The methods of the present invention can help draw links between gene expression profiles and physiological effects including a subjects' likely response to a drug candidate.

A wide variety of diseases can be detected by the process of the present invention, for example, infectious diseases caused by bacterial, viral, parasite, and fungal infectious agents. The resistance of various infectious agents to drugs can also be determined using the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Abl, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

The present invention is further illustrated by the following non-limiting examples.

EXAMPLES

Example 1—Genomic DNA Preparation

Genomic DNA is prepared from the blood of two normal human volunteers, one male and one female, according to standard techniques. Briefly, approximately 12 ml of blood is obtained in EDTA-containing blood collection tubes. Red blood cells are lysed by mixing the blood samples with 4 volumes of lysis buffer (10 mM Tris pH 8.0, 10 mM EDTA). After 10 min on ice with occasional agitation, the suspensions are centrifuged and the supernatants are decanted. The white blood cell pellets are resuspended in 20 ml of lysis buffer, and the above process is repeated. Each cell pellet is then suspended in 15 ml of digestion buffer (50 mM Tris pH 8.0, 5 mM EDTA, 100 mM NaCl, 1% SDS) and 3 mg (0.2 mg/ml) of proteinase K is added. The cells are digested at 37° C. for 5 hours. The digests are extracted twice with equal volumes of phenol, then once with equal volumes of a 1:1 phenol:chloroform mixture and finally once with equal volumes of chloroform, each time centrifuging the mixture and removing the aqueous phase for the next extraction. After the final extraction and removing the aqueous phases, one tenth volume of 3 M sodium acetate, pH 6.5, is added. Two volumes of ice cold 100% EtOH are then added to each solution to precipitate the genomic DNAs, which are spooled out of solution on glass pipettes. The DNA precipitates are washed twice in 0.75 ml volumes of 70% EtOH, briefly centrifuging each time to allow removal of the supernatants. After removing the supernatants for the second time, the remaining EtOH is allowed to evaporate and the DNA is suspended in 0.5 ml of TE (10 mM Tri-HCl pH 8.0 containing 1 mM EDTA) solution. A fifth dilution of each DNA solution is also prepared in TE.

To determine the concentrations of the one fifth DNA solutions, 1, 2, and 4 .mu.l aliquots of each are loaded on a 1% agarose gel with a known amount of HindIII digested lambda DNA as a control. The gel is run at 150 Volts for 2 hours with ethidium bromide in the electrophoresis buffer. After photographing the gel and comparing the intensities of the DNA bands, the one fifth dilutions are judged to have concentrations of approximately 100 ng/ml. DNA solutions extracted from various tumor cell lines are the generous gifts of other laboratories. The concentrations of these solutions are checked in a similar fashion and solutions of 100 ng/ml in TE are prepared.

To digest the genomic DNAs with Taq I, 25 µl of the 100 ng/µl solutions is mixed with 5 µl of 10× medium salt buffer (0.5 M NaCl, 0.1 M $MgCl_2$, 0.1 M Tris, pH 8.0), 20 µl of water-ME (i.e. water containing 6 mM ME (i.e., mercaptoethanol)), and 400 U of Taq I restriction endonuclease. The digests are covered with mineral oil and incubated at 65° C. for 1 hour. The reactions are stopped by adding 1.2 µl of 500 mM EDTA and heating the specimens to 85° C. for 10 min. Complete digestion of the DNA is checked by electrophoresing aliquots on a 1% agarose gel.

Example 2—Locus Specific Sequencing

A DNA chip containing over 10 thousand SNPs, serving as capture probes, was mixed with target polypeptide. A first solution probe was added for hybridizing with the target polypeptide. Different first solution probes were used with a difference in the base to be ligated to the SNP. At a given SNP site, the sample DNA should be a perfect match with a given probe. After a stringent wash, a first run of ligation was conducted. The chip was then washed, stained and scanned. After cleavage, through the addition of RNase, followed by phosphorylation, a second round ligation was conducted, followed by additional washing and scanning. A score, referred to as the call rate, was recorded. The call rate refers to the signal recorded of the ligation event occurring from the specific probe ligation events minus the signal from the reference probe ligation events, divided by total signal of both specific and reference probes combined. The call rate for the first round of ligation was 75% and the call rate for the second round of ligation was 45%.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of sequencing comprising:
(a) hybridizing a plurality of target polynucleotide fragments from a sample to a plurality of capture probes and a plurality of first solution probes, wherein each capture probe of the plurality of capture probes is attached to a solid support and at least one capture probe from the plurality of capture probes comprises sequence complementary to a first region of known sequence on one or more of the plurality of target polynucleotide fragments, and each first solution probe of the plurality of first solution probes are in solution and comprise a cleavage site at a 3' end and a first cap on the 3' end, and wherein at least one first solution probe of the plurality of first solution probes comprises sequence complementary to a second region of known sequence on the one or more of the plurality of target polynucleotide fragments, wherein the hybridizing comprises forming one or more hybridization complexes, wherein each of the one or more hybridization complexes comprises:

(i) a capture probe from the plurality of capture probes;
(ii) a target polynucleotide fragment from the plurality of target polynucleotide fragments; and
(iii) a first solution probe from the plurality of first solution probes, wherein the capture probe hybridizes to the first region of the known sequence on the target polynucleotide fragment and the first solution probe hybridizes to the second region of the known sequence on the target polynucleotide fragment, whereby hybridization of the capture probe to the first region and the first solution probe to the second region of the target polynucleotide fragment is configured to permit ligation of the capture probe and the first solution probe;

(b) ligating the capture probe and the first solution probe in the one or more hybridization complexes, thereby forming one or more target-capture probe-first solution probe hybridization complexes comprising the target polynucleotide fragment and ligated capture and first solution probes;

(c) adding a second cap, wherein the second cap is attached to any of the plurality of capture probes which are not ligated to any of the plurality of first solution probes;

(d) selectively removing the first cap from the one or more target-capture probe-first solution probe hybridization complexes by cleaving the cleavage site at the 3' end of the first solution probe in the one or more target-capture probe-first solution probe hybridization complexes (e) hybridizing a second solution probe to the one or more target-capture probe-first solution probe hybridization complexes from (d), wherein the second solution probe comprises sequence complementary to a third region of the known sequence on the target polynucleotide fragment, whereby the hybridizing of the second solution probe to the one or more target-capture probe-first solution probe hybridization complexes is configured to permit ligation of the second solution probe and the first solution probe;

(f) ligating the second solution probe to the first solution probe, thereby forming one or more target-capture probe-first-second solution probe hybridization complexes, comprising ligated capture probe, first solution probe, and second solution probe;

(g) hybridizing a third solution probe to the one or more target probe hybridization complexes from (f) wherein the third solution probe comprises sequence complementary to a fourth region of known sequence on the target polynucleotide fragment, and wherein the third solution probe comprises a universal primer sequence, whereby the hybridizing of the third solution probe to the target-probe hybridization complexes from (f) is configured to permit-ligation of the third solution probe and the second solution probe;

(h) ligating the third solution probe to the second solution probe, thereby generating one or more target-capture probe-first-second-third solution probe hybridization complexes comprising ligated capture probe, first solution probe, second solution probe, and third solution probe;

(i) removing the target polynucleotide fragment from the one or more target-capture probe-first-second-third solution probe hybridization complexes, thereby generating one or more single stranded complexes comprising capture probe-first solution probe-second solution probe-third solution probe polynucleotides comprising the universal primer sequence at the 3' end; and (j) determining the sequence of the one or more single-stranded complexes generated in (i) by hybridizing a primer directed against the universal primer sequence and performing a sequencing reaction.

2. The method of claim 1, wherein the sequencing reaction comprises performing a base extension reaction in the presence of labeled nucleotides.

3. The method of claim 1, further comprising removing non-specific hybridization, wherein the removing non-specific hybridization comprises performing one or more washes under stringent conditions.

4. The method of claim 1, wherein the first cap comprises a capping dye.

5. The method of claim 1, wherein the solid support is a flat surface or a bead.

6. The method of claim 5, wherein the plurality of capture probes is synthesized or spotted on said flat surface.

7. The method of claim 5, wherein the flat surface is a flow cell.

8. The method of claim 1, wherein each capture probe of the plurality of capture probes comprises 50-150 nucleotides.

9. The method of claim 1, wherein each of the first solution probes of the plurality of first solution probes comprises 5 to 50 nucleotides.

10. The method of claim 1, wherein the second, and/or third solution probe comprises 5 to 50 nucleotides.

11. The method of claim 1, wherein the first and/or second cap comprises a nucleotide reversible terminator.

12. The method of claim 1, wherein each of the plurality of first solution probes comprises a label.

13. The method of claim 1, wherein at least one of the plurality of first solution probes has at least one base that is degenerate.

14. The method of claim 1, wherein each of the plurality of target polynucleotide fragments comprises genomic DNA, and wherein the known sequence comprises a locus of interest.

15. The method of claim 14, wherein the locus of interest comprises a single nucleotide polymorphism (SNP), an insertion or deletion, or a copy number variation.

16. The method of claim 1, wherein the second and/or third solution probe comprises a label.

17. The method of claim 1, wherein the second and/or third solution probe has at least one base that is degenerate.

18. The method of claim 1, wherein at least one of the plurality of first solution probes comprises a first base at the 5' end that is degenerate.

19. The method of claim 1, wherein the second and/or third solution probes comprises a first base at the 5' end that is degenerate.

* * * * *

SEQUENCE LISTING

<160> NUMBER OF SEQ ID NOS: 56

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcgctatcg                                                          10

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atcgatccta tcg                                                      13

```
<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3 atcgmtmyyr                                                                  10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atcgctatcg                                                                  10

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcgatccta tcg                                                              13

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6 rwysctatcg                                                                  10

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
aatcaatgga catgaacaac cctcaggact ttattgattg cttcctgatg                      50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
atcaatggac atgaacaacc ctcaggactt tattgattgc ttcctgatga                      50
```

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tcaatggaca tgaacaaccc tcaggacttt attgattgct tcctgatgaa         50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
caatggacat gaacaaccct caggactttca ttgattgctt cctgatgaaa         50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
aatggacatg aacaaccctc aggactttat tgattgcttc ctgatgaaaa         50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gccctcagaa acactctggt tacctttgtg ggactcagtt tcttttgaat         50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ccctcagaaa cactctggtt acctttgtgg gactcagttt cttttgaatt         50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cctcagaaac actctggtta cctttgtggg actcagtttc ttttgaattc         50

```
<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctcagaaaca ctctggttac ctttgtggga ctcagtttct tttgaattct            50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tcagaaacac tctggttacc tttgtgggac tcagtttctt ttgaattctg            50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgaggccagc atggtggtag tgggatgata gatggtgacg gctggggtgg            50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gaggccagca tggtggtagt gggatgatag atggtgacgg ctggggtggt            50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aggccagcat ggtggtagtg ggatgataga tggtgacggc tggggtggtt            50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ggccagcatg gtggtagtgg gatgatagat ggtgacggct ggggtggttt            50

<210> SEQ ID NO 21
```

```
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gccagcatgg tggtagtggg atgatagatg gtgacggctg gggtggtttg              50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ccacagccac tgtttccaac cagggccacc gtctgcccac tctgcacctt              50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cacagccact gtttccaacc agggccaccg tctgcccact ctgcaccttc              50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
acagccactg tttccaacca gggccaccgt ctgcccactc tgcaccttca              50

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
cagccactgt tccaaccag ggccaccgtc tgcccactct gcaccttcag               50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
agccactgtt tccaaccagg gccaccgtct gcccactctg caccttcagg              50

<210> SEQ ID NO 27
<211> LENGTH: 50
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aggtgtagca atgggaggtt tagatgtcct ttcctgccag gtacacttgc          50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ggtgtagcaa tgggaggttt agatgtcctt tcctgccagg tacacttgca          50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gtgtagcaat gggaggttta gatgtccttt cctgccaggt acacttgcaa          50

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tgtagcaatg ggaggtttag atgtcctttc ctgccaggta cacttgcaaa          50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
gtagcaatgg gaggtttaga tgtcctttcc tgccaggtac acttgcaaat          50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcaacaaatc acaaattcac aagcagtcac ataactaagc ttttgtttac          50

<210> SEQ ID NO 33
<211> LENGTH: 50
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 33
caacaaatca caaattcaca agcagtcaca taactaagct tttgtttaca           50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
aacaaatcac aaattcacaa gcagtcacat aactaagctt ttgtttacat           50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
acaaatcaca aattcacaag cagtcacata actaagcttt tgtttacatt           50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
caaatcacaa attcacaagc agtcacataa ctaagctttt gtttacattt           50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
tcagtgaaat ttctcttttt gcttctagca ccgagtggat ttccttcagc           50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cagtgaaatt tctcttttg cttctagcac cgagtggatt tccttcagct            50

<210> SEQ ID NO 39
<211> LENGTH: 50
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 39
agtgaaattt ctcttttttgc ttctagcacc gagtggattt ccttcagctg              50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
gtgaaatttc tcttttttgct tctagcaccg agtggatttc cttcagctga              50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
tgaaatttct cttttttgctt ctagcaccga gtggatttcc ttcagctgat              50

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
gaggtgaaat gaggtaatta tgtaatcagc caaagtccat ccctcttttt              50

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
aggtgaaatg aggtaattat gtaatcagcc aaagtccatc cctcttttc              50

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
ggtgaaatga ggtaattatg taatcagcca aagtccatcc ctcttttca              50

<210> SEQ ID NO 45
<211> LENGTH: 50
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 45
gtgaaatgag gtaattatgt aatcagccaa agtccatccc tcttttcag            50

<210> SEQ ID NO 46
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tgaaatgagg taattatgta atcagccaaa gtccatccct cttttcagg             50

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ctgtgtctgt gaattgcctt gaagtttttt tctcactcgt cctggtagat            50

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tgtgtctgtg aattgccttg aagtttttt ctcactcgtc ctggtagatc             50

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
gtgtctgtga attgccttga agttttttc tcactcgtcc tggtagatct             50

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
tgtctgtgaa ttgccttgaa gttttttct cactcgtcct ggtagatctt             50

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic

```
<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
gtctgtgaat tgccttgaag ttttttttctc actcgtcctg gtagatcttg          50

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
aggagatgac ggcacagcag tcatatttgc aagtgtacct ggcaggaaag           50

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
ggagatgacg gcacagcagt catatttgca agtgtacctg gcaggaaagg           50

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gagatgacgg cacagcagtc atatttgcaa gtgtacctgg caggaaagga           50

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
agatgacggc acagcagtca tatttgcaag tgtacctggc aggaaaggac           50

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gatgacggca cagcagtcat atttgcaagt gtacctggca ggaaaggaca           50
```